_United States Patent_ [19]

White et al.

[11] 4,420,624

[45] Dec. 13, 1983

[54] PROCESS FOR PREPARING SPECTINOMYCIN ANALOGS

[75] Inventors: David R. White; Richard C. Thomas, both of Kalamazoo, Mich.

[73] Assignee: The Upjohn Company, Kalamazoo, Mich.

[21] Appl. No.: 359,006

[22] Filed: Mar. 17, 1982

Related U.S. Application Data

[62] Division of Ser. No. 150,530, May 16, 1980, Pat. No. 4,351,771.

[51] Int. Cl.[3] .................. C07D 327/06; C07D 327/08; C07D 323/04; C07D 319/20
[52] U.S. Cl. ...................................... 549/361; 549/16
[58] Field of Search ........................................ 549/361

[56] References Cited

PUBLICATIONS

Rosenbrook, W., et al., J. Antibiotics, vol. 31, pp. 451-455, 1978.
Rosenbrook, W., et al., J. Antibiotics, vol. 28, pp. 960-964, 1975.
Carney, R., et al., J. Antibiotics, vol. 30, pp. 960-964, 1977.
Noller, C., Chemistry of Organic Compounds, pp. 94-95, W. B. Saunder Co., Philadelphia, 1965.

_Primary Examiner_—Blondel Hazel
_Attorney, Agent, or Firm_—Sidney B. Williams, Jr.; Joan Thierstein

[57] ABSTRACT

Anomers and asteric mixtures of novel analogs of spectinomycin. Additionally provides novel intermediates and process for preparing spectinomycin and analogs thereof.

4 Claims, No Drawings

PROCESS FOR PREPARING SPECTINOMYCIN ANALOGS

BACKGROUND OF THE INVENTION

This application is a division of Ser. No. 150,530 filed May 16, 1980, U.S. Pat. No. 4,351,771.

1. Field of the Invention

The invention concerns anomers of certain novel analogs of spectinomycin including asteric mixtures thereof. The invention also includes novel intermediates for making spectinomycin analogs. Methods of making spectinomycin analogs is also within the invention.

2. Description of the Prior Art

Spectinomycin is a known antibiotic having the formula

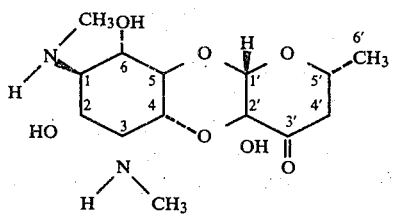

Heretofore, spectinomycin has been prepared by a microbiological process. See Bergy et al., U.S. Pat. No. 3,234,092.

Some analogs of spectinomycin are described by Rosenbrook Jr. et al., in J. Antibiotics, 28, pp. 953 and 960 (1975) and J. Antibiotics, 31, p. 451 (1978). In addition Carney et al. describes chlorodeoxy derivatives of spectinomycin in J. Antibiotics, 30, 960 (1977). Further 9-epi-4(R)-dihydrospectimomycin is reported by Foley et al., in J. Org. Cehm., 43, 22 pp. 4355–4359 (1978).

However, contrary to the present invention, biological activity is not reported for any of the spectinomycin analogs and derivatives disclosed in the above cited references.

The prior art disclosing chemical processes nearest the invention process teach a preferential reaction at the 5-hydroxyl of 2-deoxystreptamine (1) with tri-0-acetyl-2-deoxy-2-nitroso-α-D-glycopyranosyl chloride (2) to give a α-pseudodisaccharide (3) in the following manner (see Lemieux, Can. J. Chem. 51, p. 53 (1973):

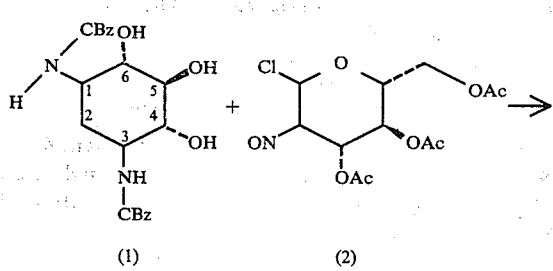

-continued

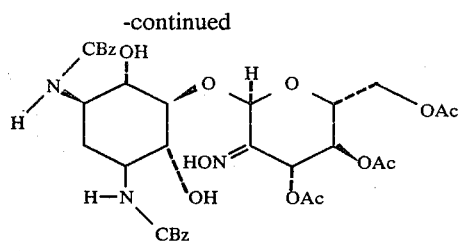

wherein CBz is carbobenzyloxy. Mallams et al., J. Chem. Soc. Perkin I, p. 1118 (1976), extend the Lemieux reaction to synthesize di- and tri-saccharides.

Removal of oximes is taught by Lemieux et al., Can. J. Chem. 51, p. 19 (1973) and Mallams et al., J. Chem. Soc. Perkin I, p. 1097 (1976).

SUMMARY OF THE INVENTION

Compounds of the invention are anomers and asteric mixtures of compounds having the formula

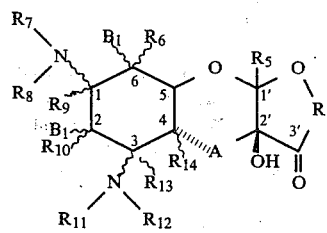

wherein R is selected from the group consisting of

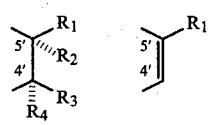

wherein $R_1$ through $R_4$ may be the same or different and are selected from the group consisting of hydrogen, lower alkyl, lower alkenyl, lower haloalkyl, lower aminoalkyl, lower alkynyl, —OX and —$(CH_2)_n$—OX with the proviso that $R_1$ and $R_2$ are not hydroxy and one of $R_3$ or $R_4$ must be hydrogen.

wherein X is selected from the group consisting of hydrogen, lower alkyl, lower alkenyl, lower alkynyl, benzyl and acyl;

n is an integer of from one to four;

$R_5$ is hydrogen or lower alkyl;

$R_6$ through $R_{14}$ are selected from the group consisting of hydrogen, lower alkyl, lower alkenyl and lower alkynyl with the proviso that one of $R_7$ and $R_8$ is always hydrogen and one of $R_{11}$ and $R_{12}$ is always hydrogen, and B and $B_1$ are the same or different and are selected from the group consisting of hydrogen, hydroxy, alkoxy, o-lower alkenyl, thio, thio lower alkyl and thio-lower alkenyl; and A is selected from the group consisting of oxygen and sulfur; with the proviso that when the compound has the formula $B_1$ cannot be hydroxy.

The numbering of carbons shown in compound I will be used in discussions thereof throughout the specification.

The compounds of this invention include the hydrate forms of compounds of formula I. These compounds are hydrated at the 3' position and having the formula

I' wherein A, B, $B_1$, R and $R_6$ through $R_{14}$ are the same as defined above. Also included are pharmaceutically acceptable salts of the compounds of formuae I and I'.

In the designation of variables herein, the group "—$(CH_2)_n$—" includes straight chain lower alkyls and isomers thereof.

"Lower alkyl" means methyl, ethyl, propyl, butyl, pentyl, hexyl, heptyl, octyl, and the isomeric forms thereof, "Lower alkenyl" means ethylidene, propylidene, butylidene, pentylidene, hexylidene, heptylidene, octylidene, and the isomeric forms thereof.

"Lower alkynyl" means ethynyl, propynyl, butynyl, pentynyl, hexynyl, heptynyl, octynyl and the isomeric forms thereof, "Lower alkoxy" means methoxy, ethoxy, propoxy, butoxy, pentoxy, hexoxy, heptoxy, octoxy and the isomeric forms thereof, "Acyl" means formyl, acetyl, propionyl, butyryl and pentionyl and isomeric forms thereof, "Aralkyl" means benzyl, phenethyl, phenopropyl, phenbutyl, phenpentyl, diphenylmethyl, diphenyloctyl and isomeric forms thereof and fluorenylmethyl, "Lower haloalkyl" means —$(CH_2)_n$-halo and isomeric forms thereof. The group contains one to three halo substituents.

"Lower aminoalkyl" means $(CH_2)_n$—N⟨lower alkyl (or H) / lower alkyl (or H)

and isomeric forms thereof,

"Aroyl" means benzoyl, substituted benzoyl, napthoyl and substituted napthoyl. The substituted benzoyls and naphthoyls may contain one to three substituents selected from the group consisting of lower alkyl, lower alkoxy, nitro and halo.

"Halogenated alkoxycarbonyl" means mono-, di-, tri-halomethoxycarbonyl; mono-, di-, tri-haloethoxycarbonyl; mono-, tri-halopropoxycarbonyl; mono-, di-, tri-halobutoxycarbonyl, mono-, di-, tri-halopentoxycarbonyl and isomeric forms thereof.

"Halo" means fluoro, chloro, bromo and iodo.

"aralkoxycarbonyl" means benzyloxycarbonyl, phenethoxycarbonyl, phenpropoxycarbonyl, phenbutoxycarbonyl, phenpentoxycarbonyl, diphenylmethoxycarbonyl, diphenyloctoxycarbonyl and isomeric forms thereof and fluorenylmethoxy carbonyl.

"Alkoxycarbonyl" means isopropyloxy carbonyl, tertiarybutyloxy carbonyl, and tertiary-pentyloxy carbonyl.

It is meant that as used in this description and in the appended claims that when more than one hydroxy or alkoxy is present on the sugar moiety herein may be the same or different.

This invention also pertains to a chemical process for preparing spectinomycin-like compounds.

Thus, the invention process realizes the importance of the stereochemistry at the glycosidic bond, i.e. 1' position of compounds of Formula I.

The term "α-anomer" means a 1' substituent below the plane of the ring system and the term "β-anomer" means a 1' substituent above the plane of the ring system. Specifically "β-anomer" means that anomers having the C-1' configuration corresponding to spectinomycin.

Compounds of this invention which exhibit desirable biological activity are β-anomers of compound I. This glycosidic configuration is found in spectinomycin. Therefore, adequate selectivity at the 1' position is desirable to obtain biologically active analogs of spectinomycin.

Actinamines and actinamine derivatives include the aminocyclitols depicted by formula VI hereafter.

"Sugars" means substituted pyrans, natural and synthetic sugars, chirals and achirals.

The process of this invention is advantageous in that is provides such selectivity in a complete chemical synthesis for antibacterial compounds which are analogs of spectinomycin. Heretofore, the prior art has not appreciated the possibility of obtaining a wide variety of spectinomycin analogs in a process which makes a six membered hemiketal of spectinomycin-like structure having biological activity by converting delta hydroxy oximes to delta hydroxy ketones.

An additional advantage of the invention process appears in that an initial actinamine reactant having protected amine groups is found to react at the C-5 hydroxy without additional protection for other β or α-hydroxyls at the C-2, C-4 or C-6 positions to produce the spectinomycin like configuration. Thus, surprisingly a difficult and combersome protection of hydroxyls not at the C-5 position on the actinamine reactant is unnecessary in the process disclosed herein. Another advantage of this invention process is the selective generation of a C-3' carbonyl, as such or in masked or latent form, by an elimination reaction. The C-3' carbonyl is an especially important but difficulty obtained feature of spectinomycin analogs.

The novel process of this invention can be represented schematically as follows:

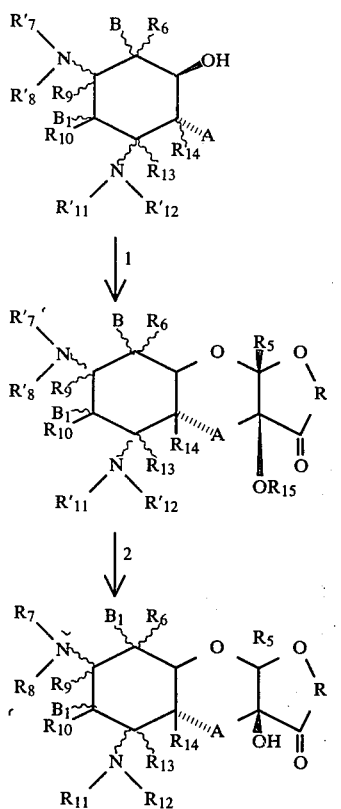

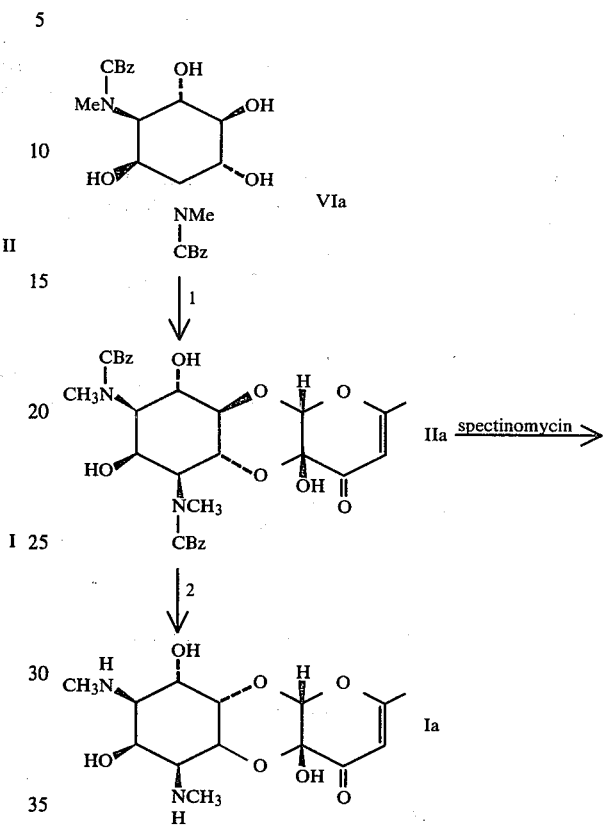

processes between VI and II are disclosed in Ser. No. 20,073, filed Mar. 13, 1979.

A more specific example of the process is as follows:

wherein R is selected from the group consisting of

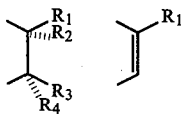

wherein $R_1$ through $R_4$ may be the same or different and are selected from the group consisting of hydrogen, lower alkyl, lower alkenyl, lower alkynyl, lower haloalkyl, lower aminoalkyl, —OX and —$(CH_2)_n$—OX with the proviso that $R_1$ and $R_2$ are not hydroxy and one of $R_3$ and $R_4$ must be hydrogen, wherein X is selected from the group consisting of hydrogen, lower alkyl, lower alkenyl, lower alkynyl, benzyl and acyl; n is an integer of from one to four; $R_5$ is hydrogen or lower alkyl; $R_6$ through $R_{14}$ are selected from the group consisting of hydrogen, lower alkyl, lower alkenyl and lower alkynyl; $R_5$ is hydrogen or lower alkyl; $R'_7$, $R'_8$, $R'_{12}$ are selected from the group consisting of lower alkyl, lower alkenyl, lower alkynyl, and a blocking group selected from the group consisting of aralkoxycarbonyl, halogenated-alkoxycarbonyl and alkoxycarbonyl; with the proviso that one of $R_7$ and $R_8$ is always hydrogen and one of $R_{11}$ and $R_{12}$ is always hydrogen, and the further proviso that one of $R'_7$ and $R'_8$ is always a blocking group and one of $R'_{11}$ and $R'_{12}$ is always a blocking group; $R_{16}$ is alkyl or aralkyl or aroyl; A is selected from the group consisting of oxygen and sulfur, and B and $B_1$ are the same or different and are selected from the group consisting of hydrogen, hydroxy, alkoxy, o-lower alkenyl, thio, thio-lower alkyl and thio-lower alkenyl. Some of the intermediates and Although both α and β anomers may be formed in step 1 of the above process, the β anomers may be preferentially obtained by the separation of β from α anomers following any step in the process. Also the utilization of an available enantiomeric sugar in the initial coupling reaction to give a high proportion of the β anomer, or epimerization of any intermediate or final product may increase the amount of β anomer obtained. Furthermore, asteric mixtures can themselves be utilized as antibacterials in as much as biological activity is present as a consequence of an active anomer therein.

"Anomers and asteric mixtures of a compound" includes analogs of spectinomycin within the invention having antibacterial activity. Although the β configuration is the active anomer of the invention, the term "anomers and asteric mixtures" is not meant to be limiting since novel α anomers may also be present without detracting from activity in an asteric mixture. Also α anomers of the spectinomycin analog may in some cases be advantageously anomerized to the active form of the analog. Therefore, the α configuration is not excluded at any step in the invention process.

On the other hand, compounds of use in the invention are products of formula I which have the β configuration because these anomers exhibit antibacterial properties. Separation of the anomers may be accomplished following any step in the process. Preferred β anomers and process of the invention are compounds including C-2 and C-6 hydroxyls having the following formulae:

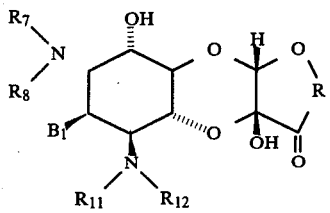

wherein all substituents are as previously designated.

Another aspect of this invention is novel intermediates in the process.

These intermediates include (i) anomers and asteric mixtures of compounds having the formula

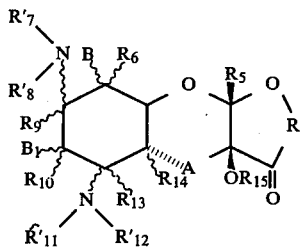

II wherein R is selected from the group consisting of

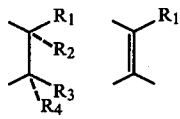

wherein $R_1$ through $R_4$ may be the same or different and are selected from the group consisting of hydrogen, lower alkyl, lower haloalkyl, lower aminoalkyl, lower alkenyl, lower alkynyl, —OX and —(CH$_2$)$_n$—OX with the proviso that $R_1$ and $R_2$ are not OH and one of $R_3$ and $R_4$ must be hydrogen, wherein X is selected from the group consisting of hydrogen, lower alkyl, lower alkenyl, lower alkynyl, benzyl and acyl;

n is an integer of from one to four, $R_5$ is hydrogen or lower alkyl;

wherein $R_6$, $R_9$, $R_{10}$, $R_{13}$ and $R_{14}$ are selected from the group consisting of hydrogen, lower alkyl, lower alkenyl and lower alkynyl; $R_5$ is hydrogen or lower alkyl; $R'_7$, $R'_8$, $R'_{11}$ and $R'_{12}$ are selected from the group consisting of lower alkyl, lower alkenyl, lower alkynyl, and a blocking group selected from the group consisting of aralkoxycarbonyl, halogenated alkoxy carbonyl and alkoxycarbonyl; with the proviso that one of $R'_7$ and $R'_8$ is always a blocking group and one of $R'_{11}$ and $R'_{12}$ is always a blocking group; $R_{15}$ is hydrogen or acyl; $R_{16}$ is lower alkyl, aralkyl or aroyl; A is selected from the group consisting of oxygen and sulfur, and B and $B_1$ are selected from the group consisting of hydrogen, hydroxy, alkoxy, o-lower alkenyl, thio, thio-lower alkyl and thio-lower alkenyl; with the proviso that when the compound has the formula

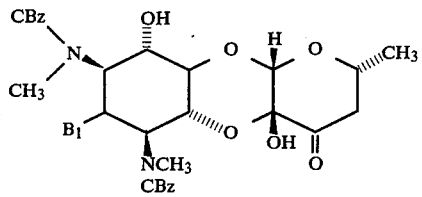

wherein CBz is carbobenzyloxy, $B_1$ cannot be hydrogen or hydroxy. (ii) anomers and asteric mixtures of compounds having the formula

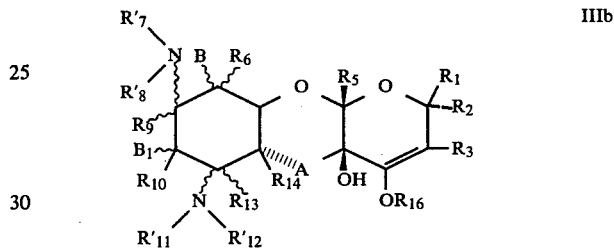

IIIb wherein A, B, $B_1$, $R_1$ through $R_3$, $R_6$, $R'_7$, $R'_8$, $R_9$, $R_{10}$, $R'_{11}$, $R'_{12}$, $R_{13}$ and $R_{14}$ are the same as above and $R_{16}$ is lower alkyl, aralkyl or aroyl, with the proviso that $R_1$, $R_2$ and $R_3$ are not hydroxy.

In compounds of formula IIIb the hemiketal may be completely or partly in the open ketonic form. These two forms may exist in equilibrium as follows:

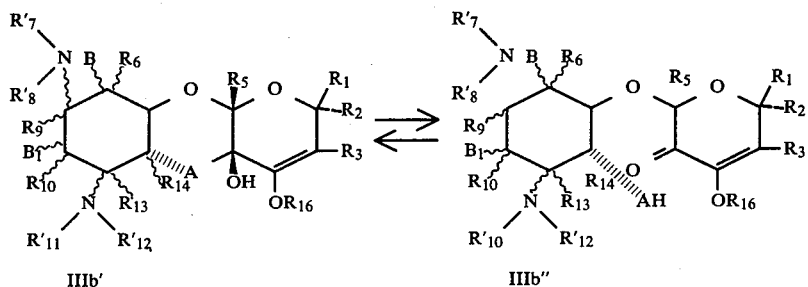

IIIb'   IIIb"

DETAILED DESCRIPTION OF THE INVENTION

Novel analogs of spectinomycin and intermediates necessary for preparation thereof can be prepared in accordance with the process outlined above. The process is also a generic method to prepare spectinomycin and a wide variety of spectinomycin analogs. Spectinomycin is an aminocyclitol antibiotic having a unique structure in that it is a single sugar component fused to an actinamine by both a β-glycosidic bond and a hemiketal bond. The method according to the invention for preparation of the analogs having this unique fusion is a synthesis which couples a sugar derivative and a protected actinamine. The sugar may be naturally derived or may be synthetic, chiral or achiral.
The process consists of two basic steps as can be seen by the schematic diagram above. Step 1 consists of the following substeps.
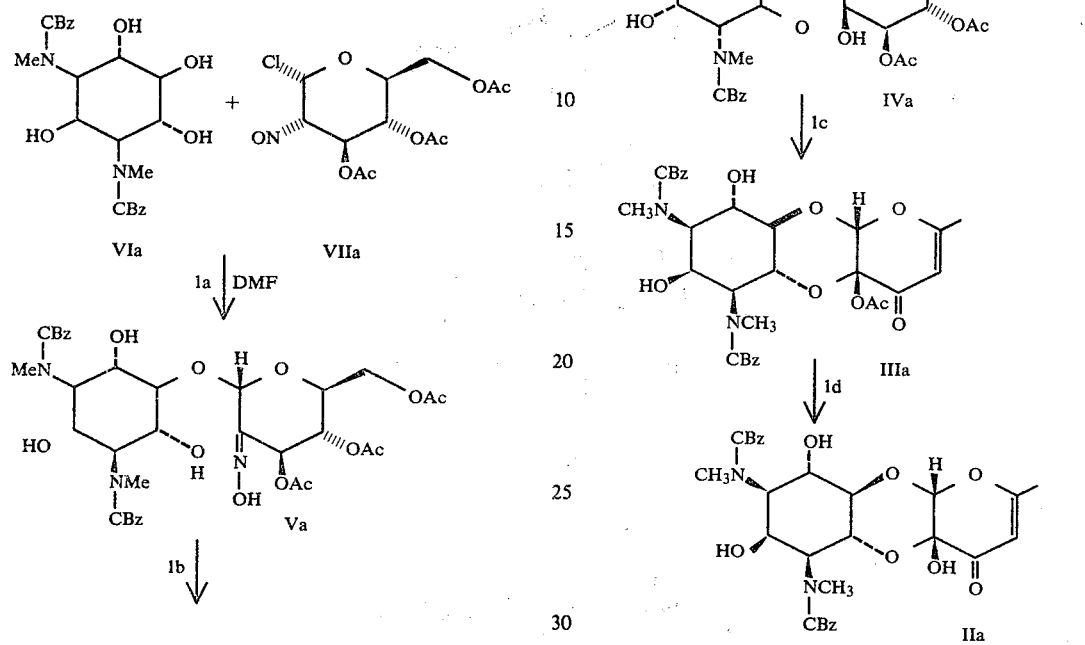
Other examples of step 1 are as follows:
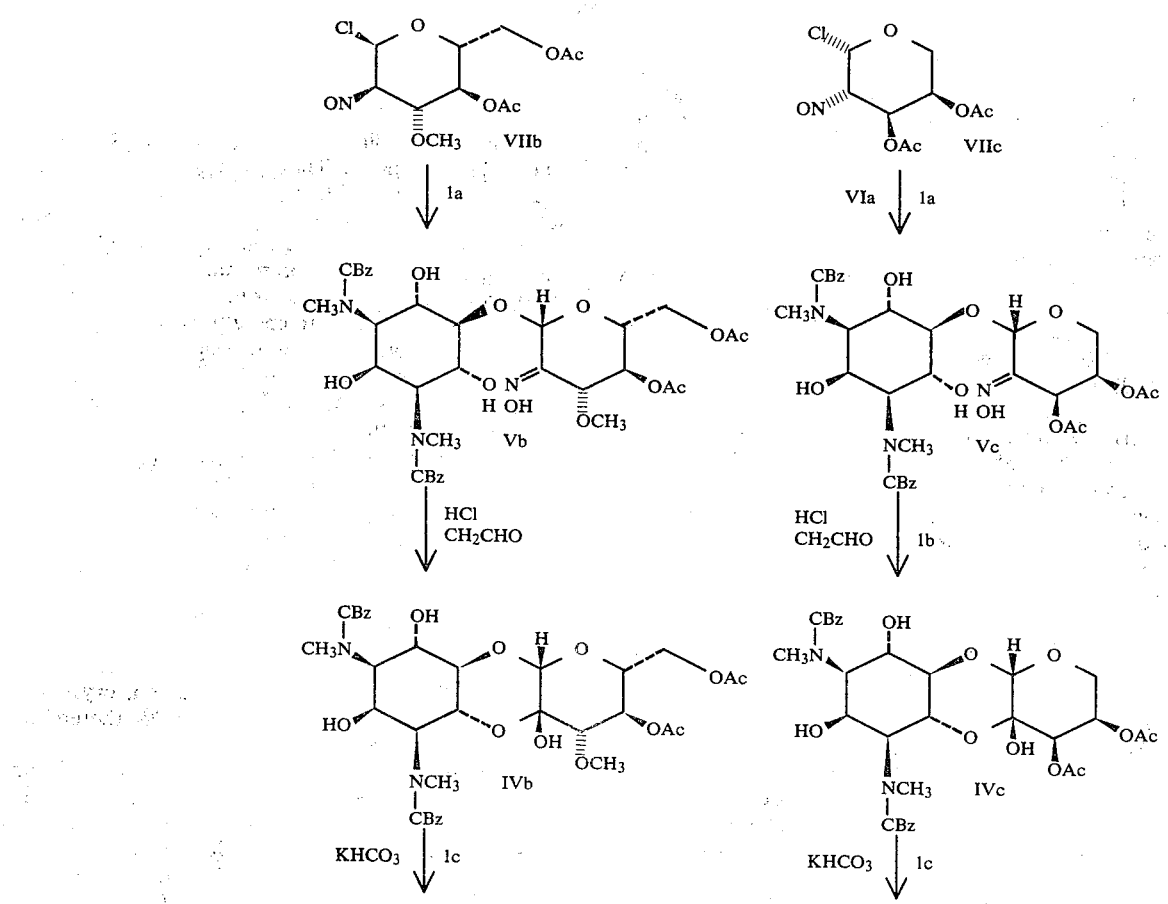

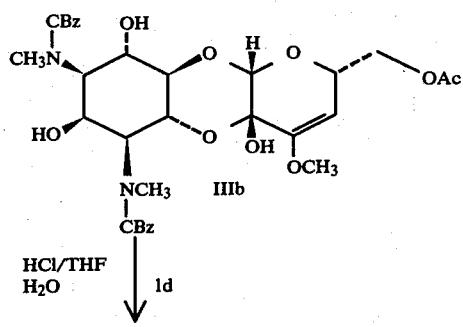
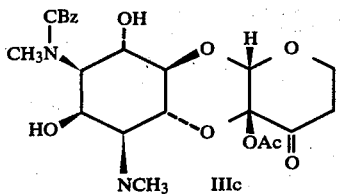
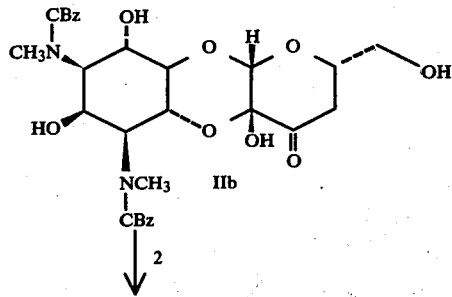
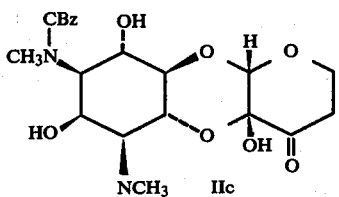
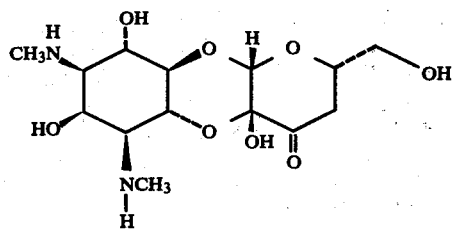
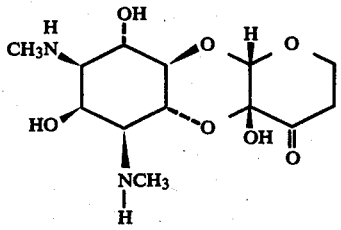

Prior to step 1a the two amino groups of the actinamine derivative VIa are protected by blocking each with a blocking group such as aralkoxycarbonyl, haloalkyloxycarbonyl, aryloxycarbonyl or alkoxycarbonyl groups which are well known in the art for this use. For example, background information on the preparation and deprotection of carbobenzyloxy and carbo-tert-butyloxy derivatives of amino acids is described by R. A. Boissonas Chapter, "Selectively Removable Amino Protective Group used in the Synthesis of Peptides.," In: Advances in Organic Chemistry, 3:159–190 (1963). Information on the use of the t-butyloxycarbonyl group to block amine is also described in ALDRICH Technical Information Bulletin entitled BOC—OH (September, 1976). Information on the use of trichloroethoxycarbonyl to block amines is disclosed by Windholz et al., Tetrahedron Letters, 2555 (1967). The actinamines can be prepared by methods well known in the art, for example see Suami et al., Bull, Chem. Soc. Jap 43, 1843 (1970).

The sugars are commercially available or can be prepared by methods known in the art; for example such a method is described by Mochalin et al., Chem Het. Comp. 699 (1977) (English translation of KHIM Geterotsiklsoedin, 867 (1977)).

Step 1a involves a coupling reaction between actinamine VI and sugar VIIa, VIIb or VIIc. This step occurs in a solution of N,N-dimethylformamide or similar solvent, such as diethyl ether, tetrahydrofuran or dimethoxymethane sometimes in the presence of a base. The reaction is most efficaciously run under nitrogen atmosphere at ambient temperatures and pressures such as described for a similar reaction by Lemieux et al., Can J. Chem. 51, 53 (1973). The temperature range of the reaction is generally 0° C. to 45° C. with molar ratios of activated sugar in solvent of 0.01 M to 0.5 M added to actinamine in a solution at a concentration of 0.01 M to 0.5 M such that in a reaction mixture the molar ratio of sugar to actinamine ranges from 0.2 to 4. Preferrable reaction conditions are a temperature of 20° C. to 30° C. using dimethylformamide as solvent with the ratio of sugar to actinamine from 3:2 to 2:3. Time of the reaction may range from 4 hours to 1 week but is preferrably from 24 to 48 hours.

The oxime Va, Vb or Vc produced is generally isolated from the reaction mixture by concentration or from concentration plus vigorous stirring with an excess of water. The resulting solid is taken up in chloroform and subsequently evaporated to dryness to yield the crude oxime intermediate. α and β anomers may be further separated into fractions by chromatography on a silica gel column eluted with methanol in chloroform in the ratio of 1:99 to 2:98. However, use of conventional recovery means such as extraction, crystallization, chromatography and combinations thereof are within the process of the invention.

Step 1b involves removal of the oxime group of compound V to form a cyclic hemiketal, compound IV above. The step 1b reaction is conducted by methods for deoximation similar to those described by Lemieux et al., in Can. J. Chem. 51, 19 (1973) and by Mallams et al., in J. Chem. Soc. Perkins I 1097 (1976). For example, in addition to the nitrogen deprotection (and C-4', C-5' saturation) which occur due to the influence of palladium catalyst and hydrogen, the C-2' acetyl is removed by alcoholsis due to the basic solvent system.

In some particular cases it is advantageous to omit step 1d or part of 1d so that the deprotection occurs in the biological system to release the active analog.

The particular conditions of the step 2 deprotection of the actinamine moiety depends upon the particular groups, i.e. group $R'_7$ or $R'_8$ and $R'_{11}$ or $R'_{12}$, that block the amine on the actinamine ring. Also by suitable choice of $R'_7$, $R'_8$, $R'_{11}$ and $R'_{12}$ and by suitable choice of deprotecting conditions known in the art, a C-4', C-5' olefin may remain intact or may be reduced during deprotection. Where that group is benzyloxy carbonyl or aralkoxy carbonyl the deprotection can be conducted under from $-10$ psi to $+200$ psi of hydrogen over a conventional catalyst such as palladium black, palladium on carbon, palladium on barium sulfate, or palladium on barium carbonate, while suspended in a solvent, for example isopropanol, absolute ethanol, ethyl acetate, toluene or tetrahydrofuran.

Alternatively, deblocking of compounds wherein $R'_7$ or $R'_8$ and $R'_{11}$ or $R'_{12}$ are alkoxycarbonyl or aryloxycarbonyl can be conducted in the presence of an acid in solvent such as nitromethane and methylene chloride.

When $R'_7$ or $R'_8$ and $R'_{11}$ or $R'_{12}$ are haloalkoxycarbonyl, the deblocking is preferably conducted in the presence of zinc.

Any method within the skill in the art may be used for isolation of an analog or asteric mixture of a compound having formula I and methods disclosed herein are not meant to be limiting. If isolation is conducted under anhydrous conditions compounds having a carbonyl group at the 3' position (formula I) are obtained. If conducted under aqueous conditions, compounds hydrated at the 3' position (formula I') are obtained. One such method includes evaporation of the excess solvent and formation of a crystalline salt of the compound. These salts may be formed using a solution of an acid as toluene sulfonic acid, hydrochloric acid, hydrobromic acid, hydroiodic acid or other acids in a solvent such as water, methanol, ethanol, isopropanol, ether, 1,2-dimethoxyethane or p-dioxane. The salt is isolated by filtration and direct crystallization or by evaporation of the solvent followed by subsequent recrystallization from a suitable solvent.

Alternatively, the crude analogs may be purified by adsorption on to a column of a weakly acidic ion exchange resin such as Amberlite IRC-50 or CG-50 followed by elution with a solvent such as water, methanol, ethanol, ether, tetrahydrofuran, 1,2-dimethoxy, 1,2-dimethoxy ethane or p-dioxane containing hydrochloric acid, hydrobromic acid, hydroiodic acid and sulfuric acid.

Similarly, the salts of hydroxy analogs may be reconverted to the free analog by passing a solution of the salt in solvent such as water, methanol, ethanol, tetrahydrofuran or 1,2-dimethoxy ethane through a basic ion exchange resin such as Dowex 1-X8 (OH—) and evaporating the eluate containing the analogs having free base substituents.

Each step of the above process can be conducted on asteric mixtures of various anomers or on the desired $\beta$ anomer itself obtained by resolution or separation at any stage in the process. The remaining steps may be conducted on $\beta$-intermediates resulting in the desired biologically active anomers.

The preferred method is to separate $\beta$ anomers from the mixture resulting from step 1 coupling of sugar and actinamine and to conduct step 2 of the process on the $\beta$ anomers producing only analogs of spectinomycin which are biologically active.

Separation of the anomers from asteric mixtures can be accomplished with modifications obvious to those skilled in the art utilizing conventional methods of resolution. For example, compound IV may be separated so as to obtain a desired $\beta$ component by chromatography on a silica gel column eluted with a mixture of methanol in chloroform in the ratio of 1:99 to 2:98. Likewise, separation of $\beta$ anomers may be effected on an asteric mixture of compound V by pooling $\beta$ fractions obtained on a silica gel chromatograph with a chloroform methanol eluent. Subsequent evaporation to dryness in vacuo yields a separated hemiketal having the $\beta$ structure.

Another particularly effective method within the invention and therefore preferred is, the obtaining of a relatively high concentration of a $\beta$ anomer in the step 1 coupling reaction by using an enantiomeric sugar favoring formation of the $\beta$ structure. For example, D-arabinose yields $\beta$ and $\alpha$ oximes in an approximately 4:1 ratio. In addition to avoiding costly and time consuming separation procedures on intermediates or resulting products to obtain the $\beta$ configuration the enantiomer may also be available in quantities which are inexpensive. Thus, use of such an enantiomer results in a recovered mixture substantially enriched in the desired $\beta$ anomer which may be brought to purity by the use of a method as described above or may be used without further purification.

Acid salts can be made by neutralizing compounds of formula I with the appropriate acid to below about pH 7.0 and advantageously to about pH 2 to pH 6. Suitable acids for this purpose include hydrochloric, sulfuric, phosphoric, sulfamic, hydrobromic, and the like. Acid and base salts of the compounds can be used for the same biological purposes as the parent compound.

The compounds of formula I inhibit the growth of microorganisms in various environments. For example, formula I compounds having the $\beta$ configuration are active against *Escherichia coli* and can be used to reduce, arrest, and eradicate slime production in papermill systems caused by its antibacterial action against this microorganism. These $\beta$ anomers also can be used to prolong the life of cultures of *Trichomonas foetus, Trichomonas hominis,* and *Trichomonas vaginalis* by freeing them of *Escherichia coli* contamination. Still further, $\beta$ anomers are active against *Bacillus subtilis* so it can be used to minimize or prevent odor in fish or fish crate caused by this organism. Also the anomers can be used to swab laboratory benches and equipment in a mycological laboratory. $\beta$-anomers are also effective against *Klebsiella pneumoniae*.

The compounds of formual I are also effective for treating bacterial infections, such as gonorrhea, and tumors in mammals, including humans.

The compositions of the present invention are presented for administration to humans and animals in unit dosage forms, such as tablets, capsules, pills, powders, granules, sterile parenteral solutions or suspensions, eye drops, oral solutions or suspensions, and water-in-oil emulsions containing suitable quantities of the compound of formula I.

For oral administration, either solid or fluid unit dosage forms can be prepared. For preparing solid compositions such as tablets, the compound of FIG. 1 is mixed the deoximation reaction is conducted by dissolving either the crude oxime or the separated α and β oximes of compound V in a solvent with subsequent addition of acetaldehyde and hydrochloric acid. Initial concentration of oxime in solvent is from 0.01 M to 1.5 M, but preferably 0.1 M to 0.3 M and the molar ration of the aldehyde to the oxime is from 1:1 to 80:1. 1 N hydrochloric acid is added in about a 2:3 ratio with the oxime. The reaction mixture is stirred at room temperature for from 3.75 hours to 5 days at which time sodium bicarbonate may be added with an additional 15 minutes of stirring. Alternatively the concentrate may be chromatographed directly such that silica gel removes HCl during purification.

Intermediate IV is recovered by conventional means as described above. One suggested recovery is by preparation of a filtrate which is evaporated to dryness in vacuo to yield the crude product. Again this product may be repeatedly fractionated on a silica gel chromatograph using a chloroform-methanol eluent in about a 95:5 ratio. Pooling of similar fractions consistent with thin layer chromatographic analysis thereof and subsequent evaporation to dryness in vacuo yields separate α and β anomers of hemiketal encompassed by structural formula IV.

Bases other than sodium bicarbonate can be used in step 1b deoximation; however, maintaining the lack of hydrolytic conditions is critical at this stage to prevent diversion away from the cyclized intermediates which are stable and useful in making analogs within the invention. Therefore, bases used must be those that will not attack acetates, i.e. hydroxides cannot be used in excess. Useful examples include benzoates or dipotassium hydrogen phosphate.

Solvents that may be used include acetonitrile, tetrahydrofuran, ether or dimethylformamide. The preferred solvent is acetonitrile.

Step 1c both removes one or two substituents on the sugar moiety of compound IV and generates a C-3′ carbonyl by β-elimination from the C-4′ position to yield the compound of formula III. A second elimination may occur from C-6′ to yield a C-4′, C-5′ olefin. This step is conducted in the presence of a base system at temperatures from about 0° to 80° C. for a period of from about 2 hours to 1 week. Base systems that can be used includes potassium bicarbonate, triethylamine, pyridine and alkoxide. A preferred system is potassium bicarbonate/acetonitrile. One to 20 mole equivalents of base may be used but 1 to 10 is preferred.

The way in which step 1c is accomplished also depends upon the particular protective groups on the sugar moiety as well as on the actinamine moiety of intermediate IV. In general the protective groups on the sugar moiety are less difficult to remove than those on the actinamine moiety. Step 1c is a novel process for mild and selective generation of the important C-3′ carbonyl as such or in latent form, by elimination.

The C-4′ and C-6′ derivatives which may undergo elimination are described in U.S. application Ser. No. 20,073, filed Mar. 13, 1979. For example, acetates eliminate acetic acid, benzoate, benzoic acid, benzyl ethers eliminate benzyl alcohol, halides eliminate hydrogen halide. These are non-limiting examples of elimination occurring in step 1c.

The intermediates of this invention, especially the products of step 1c are useful materials for synthesis of a variety of analogs. This is done by changing functional groups of the intermediates by known methods such as halogenation, reduction, oxidation, chain extension and the like. The nature of the substitutions on the intermediates are determined by the specific actinamines and sugars used as starting materials.

In some cases of this invention the elimination step 1c is accompanied by migration of the C-3′ substituent on oxygen to the C-2′ oxygen with generation of a C′3′ carbonyl. This behavior is exemplified in conversion of IVa to IIIa and IVc to IIIc. In other cases the C-3′ substituent on oxygen does not migrate such that a masked or latent C-3′ carbonyl is formed; these are enol derivatives. An example is the conversion of IVb to IIIb. The enol derivatives can exist as hemiketals or open ketonic isomers or as mixtures of these forms.

Both of the above cases are novel, useful, selective methods ultimately giving spectinomycin analogs with C-3′ carbonyl groups. The masked or latent C-3′ carbonyl containing intermediates have unique chemical properties which make them useful for modification by known methods such as halogenation, alkylation, acylation, oxidation and the like. Finally the masked or latent C-3′ carbonyl group is much more stable especially to base so that it is part of more versatile and more easily isolated intermediates.

The compound of formula III is removed from the reaction mixture by conventional methods such as precipitation, crystallization or concentration followed by chromatography.

Step 1d involves deprotection at one or several of the sugar ring positions. Usually these are C-2′, C-3′ or C-6′ and depending on the nature of the protecting groups acid and/or base may be used. When base is used as with conversion IIIa to IIa or IIIc to IIc, hydrolysis is conducted at −10° to 50° for a period of 5 minutes to 40 hours. The preferred conditions are 20°-30° for 1 to 20 hours.

Alcohols that can be used include methanol, ethanol and isopropanol, but methanol is preferred. Any base that does not degrade the product can be utilized. This includes sodium bicarbonate, potassium bicarbonate, pyridine, dipotassium hydrogen phosphate, triethylamine, sodium potassium tartrate, but the preferred catalyst is dipotassium hydrogen phosphate. In the first step of a two step process to convert IIIb′ to IIb the C-6′ acetyl group is removed selectively by the above basic alcoholysis conditions while the C-3′ methoxy group remains intact.

Acid catalysis can also be used to remove the protecting groups of the sugar ring. For example, after the C-6′ acetyl has been removed from IIIb′ by using base as described above the remaining C-3′ protection may be removed by subsequent acid treatment to give IIb. Alternatively, IIIb′ may be converted to IIb in one step using acid catalysis.

Acid mediated deprotection is usually done at 0° to 80° preferably at 20°-30° for a period of 1 hour to 3 days, preferably 2 hours to 2 days. Acids used in the art such as hydrochloric, paratoluene sulfuric or phosphoric acids may be used; preferably hydrochloric acid is used. Solvents may include aqueous tetrahydrofuran, aqueous dimethoxyethane, methanol or ethanol. Preferably methanol or aqueous tetrahydrofuran are used.

In some cases it is advantageous to combine step 1d with step 2 by using a reaction medium for step 2 which fulfills the deprotection conditions specified for step 1d above. For example, when step 2 is conducted in isopropanol with added pyridine, intermediate IIIa is converted to the antibiotic spectinomycin. This shows that with conventional ingredients such as talc, magnesium stearate dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule an sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Additionally, a rectal suppository can be employed to deliver the active compound. This dosage form is of particular interest where the mammal cannot be treated conveniently by means of other dosage forms, such as orally or by insufflation, as in the case of young children or debilitated persons. The active compound can be incorporated into any of the known suppository bases by methods known in the art. Examples of such basis include cocoa butter, polyethylene glycols (Carbowaxes), polyethylene sorbitan monostearate, and mixtures of these with other compatible materials to modify the melting point or dissolution rate. These rectal suppositories can weight from about 1 to 2.5 Gm.

The term "unit dosage form" as used in the specification refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are tablets, capsules, pills, suppositories, powder packets, wafers, granules, cachets, teaspoonfuls, tablespoonfuls, dropperfuls, ampoules, vials, aerosols with metered dicharges, segregated multiples of any of the foregoing, and other forms as herein described.

An effective quantity of the compound is employed in treatment. The dosage of the compound for treatment depends on many factors that are well known to those skilled in the art. They include for example, the route of administration and the potency of the particular compound. A dosage schedule for humans of from about 2 to about 4000 mg of compound in a single dose, administered parenterally or in the compositions of this invention, are effective for treating tumors and bacterial infections. More specifically, the single dose is from 5 mg to about 200 mg of compound. The oral and rectal dose is from about 5 mg to about 5000 mg in a single dose. More specifically, the dose is from about 10 mg to about 2500 mg of compound.

The following described preparations of analogs of spectinomycin and intermediates useful in the preparation thereof are indicative of the scope of this invention and are not to be construed as limitative. Those skilled in the art will promptly recognize variations from the procedures both in the analogs and analog precursors within the novel compounds described as well as reaction conditions and techniques of the invention process.

For example, for each of the Preparations and Examples in the following descriptions, corresponding stereoisomers for each named compound is contemplated to be within the scope of the invention.

Preparation 1

5-O-(3',4'-di-O-acetyl-2'-deoxy-2'-oximino-D-arabinopyranosyl)-N,N'-dicarbobenzyloxyactinamine

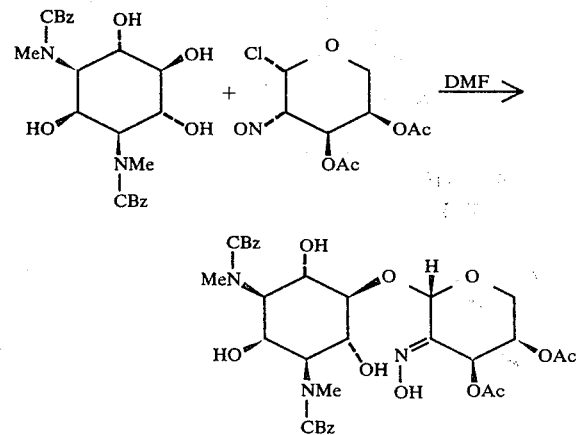

To a solution of 7.20 g (27.10 mmol) of 3,4-di-O-acetyl-2-deoxy-2-nitroso-β-D-arabinopyranosyl chloride in 75 ml of dimethylforamide is added a solution of 11.86 g (25.0 mmol) of N,N'-bis-carbobenzyloxyactinamine in 50 ml of dimethylformaide. The reaction mixture is stirred 19.5 hours at room temperature under a nitrogen atmosphere. The mixture is poured into 1 liter of water with vigorous stirring. The aqueous phase is decanted and the solid is taken up in 300 ml of chloroform, the small amount of water is separated and the solvent is removed in vacuo to give 12.6 g of a brittle white foam. The total aqueous phase is extracted three times with 100 ml portions of chloroform. The combined organics are washed with water and brine (50 ml each) and dried over sodium sulfate. The solvent is reduced to 40 ml and this solution is added to 300 ml of water with stirring. The small chloroform layer is separated and the solvent is removed in vacuo to give 6.18 g of white foam which is combined with the other portion. Analysis of the crude product by PMR showed that most of the DMF had been removed by this procedure. Chromatography on 1.25 kg of silica gel (methanol chloroform gradient) affords 1.33 g (1.89 mmole, 7.6 percent) of the pure α-anomer of 5-O-(3'-4'-O-acetyl-2'-deoxy-2'-oximino-D-arabinopyranosyl)-N,N'-dicarbobenzyloxyactinamine, followed by 2.86 g of the pure β-anomer of 5-O-(3',4'-di-O-acetyl-2'-deoxy-2'-oximino-D-arabinopyranosyl)-N,N'-dicarbobenzyloxyactinamine and another 3.17 g of said β-anomer having about 90 percent purity.

For the α-anomer: IR (CHCl$_3$) 3550, 3400, 3070, 2980, 1745, 1686, 1675 (sh), 1484, 1449, 1364, 1333, 1235, 1167, 1026, 669 cm$^{-1}$; PMR (CDCl$_3$) δ7.40 (s, 10, aromatic) 6.07 (s, 1, H$_1$'), 5.95 (d, J=3 Hz, 1, H$_3$') 5.20 (m, 7), 3.3–4.6 (m, 10), 3.12 and 3.08 (s's, 6, NCH$_3$), 2.12 and 2.03 (s's, 6, CH$_3$); MS (for tetra trimethylsilyl derivative) 991 (M+), 689, 673: CMR (d$_6$-acetone) δ170.1, 169.8, 157.8, 156.5, 150.1, 138.1, 129.1, 128.8, 128.4, 91.7, 86.9, 79.1, 74.4, 69.1, 68.6, 68.3, 67.8, 67.3, 60.3, 57.7, 31.5, 31.4, 20.8, 20.5; mp 130°–140°, decomposition. High resolution MS (tetra TMS) C$_{45}$H$_{73}$N$_3$O$_{14}$Si$_4$ requires 991.4169; found: 991.4190.

For the β-anomer: IR (CHCl$_3$) 3500, 3100, 2970, 1748, 1686, 1672 (sh), 1486, 1449, 1370, 1337, 1235, 1167, 1107, 1024, 700 cm$^{-1}$; PMR (CDCl$_3$) δ7.40 (s, 10, aromatic), 6.40 (s, 1, H$_1$') 6.05 (d, J=3 Hz, 1, H$_3$'), 5.0–5.5 (m, 6), 3.4–3.8 (m, 11), 3.07 and 3.04 (s's, 6, NCH$_3$), 2.08, 2.05 (s's, 6, CH$_3$); MS (for tetratrimethylsilyl derivative), 991 (M+), 990, 976, 975, 689, 673; CMR (d$_6$-acetone) δ170.7, 169.9, 157.7, 157.1, 149.1, 137.9, 129.1, 128.7, 128.3, 92.3, 85.3, 74.7, 70.8, 69.4, 67.3, 62.0, 60.2, 31.4, 20.8, 20.5; mp 140°–155° decomposition. High resolution MS (tetra TMS) C$_{45}$H$_{73}$N$_3$O$_{14}$Si$_4$ requires 991.4169; found 991.4229.

Preparation 1a

5-O(3',4',6'-Tri-O-acetyl-2'-oximino-2'-deoxy-α-L-glucopyranosyl)-N,N'-dicarbobenzyloxyactinamine

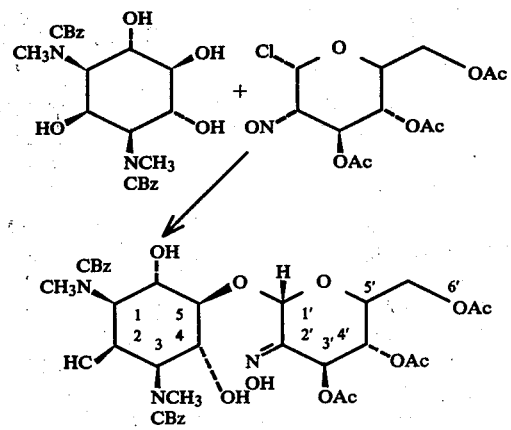

A solution of 3,4,6-tri-O-acetyl-2-nitroso-2-deoxy-α-L-glucopyranosyl chloride (7.09 g, 21 mmole) in 150 ml dimethylformamide and N,N-dicarbobenzyloxyactinamine (14.22 g, 30 mmole) is stirred for 19 hours after which time none of the pyranosyl chloride remains. The solution is concentrated at 45° and the residue dissolved in chloroform containing 1.5 percent methanol. This residue is placed on a column of wet packed silica gel (3 kg). The column is eluted with solvent (1.5 percent methanol in chloroform). After about 10 l. of solvent are used, the main product is eluted as judged by TlC (5 percent methanol in chloroform). The fractions containing pure product are combined and concentrated to yield 7.86 g (48 percent) of 5-O-(3',4'-6'-tri-O-acetyl-2'-oximino-2'-deoxy-α-L-glucopyranosyl)N,N'-dicarbobenzyloxyactinamine.

CD (CH$_3$OH) [θ]$_{926}$ m$\mu^{max}$+18,900±1,300
[α]$_D^{25}$−53° (C, 0.9 acetone)
FMR(CDCl$_3$): 2.02 (9H,S), 3.03 (6.H,S), 5.04 (4H,S), 6.20 (1H,S) 7.328 (10H,S)
CMR (CD$_3$COCD$_3$): 170.8, 170.0, 169.8, 157.7, 157.0, 149.5, 137.9 129.1, 128.7, 128.3, 92.0, 85.8, 74.4, 70.4, 69.8, 69.4, 68.6, 67.3, 62.5, 60.6, 60.2, 31.4, 31.1, 20.6 ppm.
Mass spectrum, m/e (tetra TMS): 1063 (M+), 1048, 793, 792, 689, 674, 645.

PREPARATION 1b

5-O-(4',6'-di-O-acetyl-3'-O-methyl-2'-deoxy-2'-oximino-β-D-glucopyranosyl)-N,N'-dicarbobenzyloxyactinamine

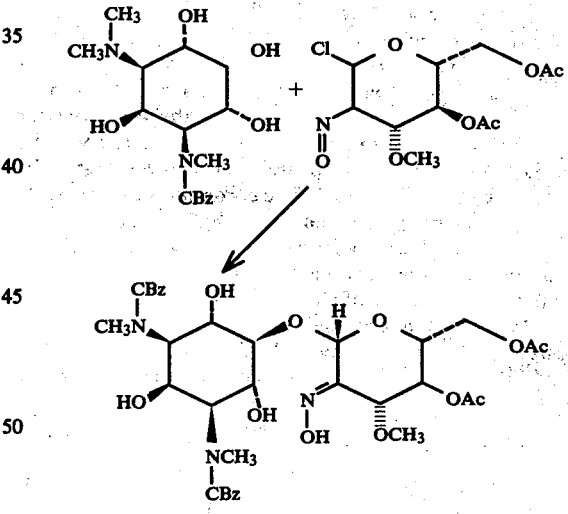

To a solution of 60.8 g (196 mmoles) of 4,6-di-O-acetyl-3-O-methyl-2-nitroso-α-D-glucopyranosyl chloride (2) in 1.1 liter of dimethylformamide is added 97.7 g (201 mmoles) N,N'-bis-carbobenzyloxy actinamine. The reaction is stirred for 45 hours at room temperature under a nitrogen atmosphere and then concentrated at 30° C. under high vacuum to give a thick syrup. This is poured in portions into a total of 3 liter of chilled water vigorously stirred. The resulting white solid is filtered, redissolved in 3 liters of chloroform separated from the residual water and dried over sodium sulfate. Concentration of chloroform layer gives 143 g of a sticky white foam containing approximately 7 percent dimethylformamide by NMR integral ratios.

Chromatography on 3.5 kg of silica gel using methanol:chloroform gradient elution system gives a rough separation of products. Fraction containing the β-anomer are crystallized from acetone to give 4.4 g of the pure β isomer. Chromatography of the mother liquors gives an additional 1.5 g of the β-anomer.

IR: 3500, 3310, 2920, 1750, 1690, 1459, 1240, 1175, 1105, 1403, 735, 711 cm$^{-1}$.

PMR (CDCl$_3$) 7.32s, 5.41s, 5.11s, 3.5–4.5m, 3.33s, 3.04s, 2.02s.

CMR (CDCl$_3$) 170.6, 169.6, 157.7, 156.5, 150.1, 136.5, 1.28.5, 127.8, 95.7, 92.7, 77.1, 73.2, 70.1, 67.54, 64.0$_9$, 56.8, 29.7, 20.8, 20.5 ppm.

Mass spec. (tetra-trimethylsilyl derivative) M+ 1035 mp. 214°–216°.

Utilizing a procedure similar to Preparation 1, 1a and 1b but substituting the appropriately-substituted actinamine and sugar reactants, there are obtained the oxime of Tables I and II.

TABLE I

| B | B$_1$ | R"$_1$ | R"$_2$ | R"$_3$ | R"$_4$ | R"$_{15}$ |
|---|---|---|---|---|---|---|
| HO— | HO— | H— | CH$_3$COCH$_2$— (O) | CH$_3$CO— (O) | H | CH$_3$O— (O) |
| CH$_3$O— | HO— | " | " | " | " | " |
| C$_2$H$_5$O— | HO— | " | " | " | " | " |
| HS— | HO— | " | " | " | " | " |
| CH$_3$S— | HO— | " | " | " | " | " |
| C$_2$H$_5$S— | HO— | " | " | " | " | " |
| H— | HO— | " | " | " | " | " |
| HO— | H— | " | " | " | " | " |
| HO— | CH$_3$O— | " | ClCH$_2$— | " | " | " |
| HO— | HO— | " | BrCH$_2$— | " | " | " |
| HO— | HS— | " | ClCH$_2$— | " | " | " |
| HO— | CH$_3$S— | " | BrCH$_2$ | " | " | " |
| HO— | C$_2$H$_5$S— | " | ClCH$_2$— | " | " | " |
| HO— | HO— | " | PhCH$_2$OCH$_2$— | PhCH$_2$O— | H— | PhCH$_2$— |
| HO— | " | " | PhCH$_2$O— | " | " | " |
| HO— | " | " | CH$_3$O— | CH$_3$C—O— (O) | " | CH$_3$C— (O) |
| HO— | " | " | C$_2$H$_5$— | H | " | " |
| HO— | " | " | CH$_3$C—OCH$_2$— (O) | CH$_3$C—O— (O) | CH$_3$OCH$_2$— | " |
| HO— | " | " | " | " | C$_2$H$_5$— | " |
| HO— | " | CH$_3$OCH$_2$— | H | " | H | " |
| HO— | " | PhCH$_2$OCH$_2$— | " | " | " | PhCH$_2$— |
| HO— | " | H— | H— | CH$_3$O | H | CH$_3$— |
| HO— | " | " | CH$_3$C—O—CH$_2$— (O) | CH$_3$C—O— (O) | " | CH$_3$— |

TABLE II

| B | B₁ | R"₁ | R"₂ | R"₃ | R"₄ | R"₁₅ |
|---|---|---|---|---|---|---|
| HO— | HO— | H— | CH₃COCH₂— (C=O) | CH₃CO— (C=O) | H | CH₃C— (C=O) |
| CH₃O— | HO— | " | " | " | " | " |
| C₂H₅O— | HO— | " | " | " | " | " |
| HS— | HO— | " | " | " | " | " |
| CH₃S— | HO— | " | " | " | " | " |
| C₂H₅S— | HO— | " | " | " | " | " |
| H— | HO— | " | " | " | " | " |
| HO— | H— | " | " | " | " | " |
| HO— | CH₃O— | " | ClCH₂— | " | " | " |
| HO— | HO— | " | BrCH₂ | " | " | " |
| HO— | HS— | " | " | " | " | " |
| HO— | CH₃S— | " | " | " | " | " |
| HO— | C₂H₅S— | " | " | " | " | " |
| HO— | HO— | " | ⟨Ph⟩CH₂OCH₂— | ⟨Ph⟩CH₂O— | H— | ⟨Ph⟩CH₂— |
| HO— | " | " | ⟨Ph⟩CH₂O— | " | " | " |
| HO— | " | " | CH₃O— | CH₃C—O— (C=O) | " | CH₃C— (C=O) |
| HO— | " | " | C₂H₅— | H | " | " |
| HO— | " | " | CH₃C—OCH₂— (C=O) | CH₃C—O— (C=O) | CH₃OCH₂— | " |
| HO— | " | " | " | " | C₂H₅— | " |
| HO— | " | CH₃OCH₂— | H | " | H | " |
| HO— | " | ⟨Ph⟩CH₂OCH₂— | " | " | " | ⟨Ph⟩CH₂— |
| HO— | H | H— | CH₃OCH₂— (C=O) | H | H | CH₃— |

PREPARATION 2

N,N'-dicarbobenzyloxy-5'-demethyl-3'-O-acetyl-4'-(R)-acetoxy-3"(R)-dihydrospectinomycin

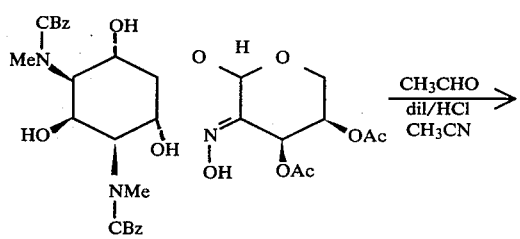

5-O-(3',4'-O-acetyl-2'-deoxy-2'-oximino-D-arabinopyranosyl)-N,N'-dicarbobenzyloxyactinamine (2.32 g, 3.30 mmol) is dissolved in 30 ml of methylnitrile and 5.0 ml (89.4 mmol) of acetaldehyde and 2.5 ml (2.50 mol) of 1 N hydrochloric acid are added. The reaction mixture is stirred 3.75 hours at room temperature, sodium sulfate is added and stirring is continued for 15 minutes. The mixture is filtered and solvent is removed in vacuo to afford 2.6 g of white solid. Chromatography on 200 g of silica gel (methanol:chloroform) gives 1.45 g (2.11 mmol, 64 percent of N,N'-dicarbobenzyloxy-5'-demethyl-3'-O-acetyl-4'-(R)-acetoxy- 3'(R)-dihydrospectinomycin as white solid:

mp 135.0–142.9°.

IR (CHCl$_3$) 3450, 3050, 1748, 1684, 1881, 1447, 1362, 1333, 1238, 1160, 1050, 1020, 680 cm$^{-1}$: PMR (CDCl$_3$) δ 7.4 (s, 10, aromatic), 3.4–5.4 (m), 3.05 (s, 6, NCH$_3$), 2.10 (s, 3, COCH$_3$), 1.95 (s, 3, COCH$_3$);

CMR (d$_6$-acetone) δ170.2, 169.8, 157.5, 156.9, 138.0, 129.1, 128.3, 94.6, 91.5, 74.7, 72.4, 67.3, 67.0, 66.3, 65.6, 61.7, 61.2, 57.5, 31.6, 20.6; MS (for tris trimethylsilyl derivative) 904 (M+).

PREPARATION 2a

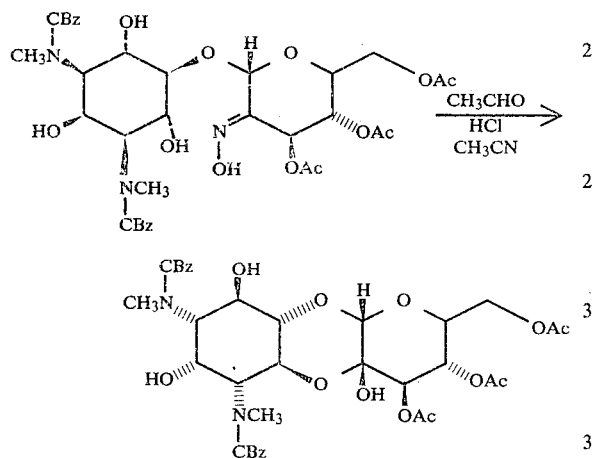

A solution of 5-O-(3',4',6'-tri-O-acetyl-2'-oximino-2'deoxy-α-L-gluco-pyranosyl)N,N'-dicarbobenzyloxyactinamine (7.00 g, 9.03 mmole), acetonitrile (7 ml) acetaldehyde (14.2 ml) and 1N HCl 17.0 ml) is stirred at room temperature for 5 hours. Anhydrous sodium sulfate (60 ml) is added and stirred for 10 minutes. The solid is filtered and washed with acetonitrile. The filtrate is concentrated, taken up on chloroform-ethylacetate (1:1) (15 ml) and chromatographed on silica gel (150 g) using the same solvent. The eluate is evaluated by TLC (5 percent methanol in chloroform) and pure fractions are combined and concentrated to give 5.96 g (87 percent) of hemiketal triacetate.

$[α]_D^{27}$ –52°(C, 0.7) chloroform

PMR (CDCl$_3$): 2.06 (9H, S) 2.88 (3H, S), 3.0$_8$ (3H, S) 4.90 (s), 5.13 (4H, S), 7.38 δ (1OH, S)

CMR (CD$_3$CO CD$_3$): 170.1, 169.4, 137.5, 137.4, 128.6, 127.9, 99.2, 94.0, 82.2, 73.9, 70.6, 68.4, 68.0, 66.8, 65.6, 62.3, 60.4, 57.3, 30.0, 20.0 ppm.

PREPARATION 2b

N,N'-dicarbobenzyloxy-3'-O-methyl-4'-(R)-6'-diacetoxy-3'-(S)-dihydrospectinomycin

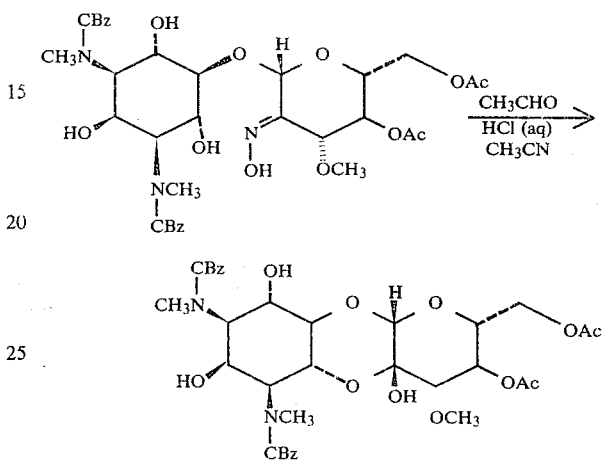

To a suspension of 5-O-(4',6'-di-O-acetyle-3'-O-methyl-2'-deoxy-2'-oximino-β-D-glucopyranosyl)-N,N'-dicarbobenzyloxy actinamine, 300 mg (0.40 mmoles) in 12 ml of acetonitrile is added acetaldehyde 1.2 ml and hydrochloric acid 0.18 ml (1.0 N), and stirred for 60 hours. The homogeneous solution is stirred with sodium sulfate for 20 minutes and filtered. Chromatography of the product on 10 g of silica gel in 15 percent chloroform/ethyl-acetate gave 150 mg of N,N'-dicarbobenzyloxy-3'-O-methyl-4'-(R)-6'diacetoxy-3'-(S)-dihydrospectinomycin.

PMR (CDCl$_3$) 7.32 s, 5.1 s, 4.68 s, 3.5 s, 3.1, 2.1 δ,

CMR (d$_6$-acetone) 171.0, 170.3, 157.8, 138.2, 129.2, 128.5, 95.8, 93.8, 84.5, 75.2, 73.1, 69.8, 67.4, 66.4, 65.2, 63.7, 61.2, 57.9, 57.5, 30.8, 29.8, 2.10, 20.7 ppm.

Mass spec. (tri-trimethylsilyl derivative) m/e (M+) 948 (M-15) 933.

Using a procedure similar to that of Preparation 2 or 2a but substituting the appropriately substituted precursor oxime from Tables I and II, there is obtained the protected spectinomycin analogs of Tables III and IV.

TABLE III

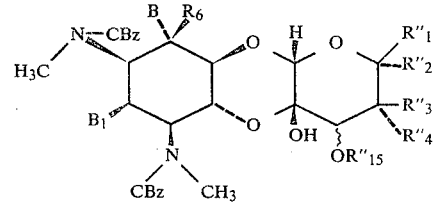

| B | B$_1$ | R"$_1$ | R"$_2$ | R"$_3$ | R"$_4$ | R"$_15$ |
|---|---|---|---|---|---|---|
| HO— | HO— | H— | $\underset{\text{CH}_3\text{COCH}_2-}{\overset{\text{O}}{\underset{\|}{}}}$ | $\underset{\text{CH}_3\text{CO}-}{\overset{\text{O}}{\underset{\|}{}}}$ | H | $\underset{\text{CH}_3\text{C}-}{\overset{\text{O}}{\underset{\|}{}}}$ |
| CH$_3$O— | HO— | " | " | " | " | " |
| C$_2$H$_5$O— | HO— | " | " | " | " | " |

TABLE III-continued

| B | B₁ | R″₁ | R″₂ | R″₃ | R″₄ | R″₁₅ |
|---|---|---|---|---|---|---|
| HS— | HO— | " | " | " | " | " |
| CH₃S— | HO— | " | " | " | " | " |
| C₂H₅S— | HO— | " | " | " | " | " |
| H— | HO— | " | " | " | " | " |
| HO— | H— | " | " | " | " | " |
| HO— | CH₃O— | " | " | " | " | " |
| HO— | C₂H₅ | " | " | " | " | " |
| HO— | HS— | " | " | " | " | " |
| HO— | CH₃S— | " | " | " | " | " |
| HO— | C₂H₅S— | " | " | " | " | " |
| HO— | HO— | " | C₆H₅CH₂OCH₂— | C₆H₅CH₂O— | H— | C₆H₅CH₂— |
| HO— | " | " | C₆H₅CH₂O— | " | " | " |
| HO— | " | " | CH₃O— | CH₃C(O)—O— | " | CH₃C(O)— |
| HO— | " | " | C₂H₅— | H | " | " |
| HO— | " | " | CH₃C(O)—OCH₂— | CH₃C(O)—O— | CH₃OCH₂— | " |
| HO— | " | " | " | " | C₂H₅— | " |
| HO— | " | CH₃OCH₂— | H | " | H | " |
| HO— | " | " | C₆H₅CH₂OCH₂— | " | " | C₆H₅CH₂— |
| HO— | " | H | CH₃COCH₂C(O) | " | " | CH₃— |

TABLE IV

| B | B₁ | R″₁ | R″₂ | R″₃ | R″₄ | R″₁₅ |
|---|---|---|---|---|---|---|
| HO— | HO— | H— | CH₃COCH₂C(O)— | CH₃CO— | H | CH₃C(O)— |
| CH₃O— | HO— | " | " | " | " | " |
| C₂H₅O— | HO— | " | " | " | " | " |
| HS— | HO— | " | " | " | " | " |
| CH₃S— | HO— | " | " | " | " | " |
| C₂H₅S— | HO— | " | " | " | " | " |
| H— | HO— | " | " | " | " | " |
| HO— | H— | " | " | " | " | " |
| HO— | CH₃O— | " | " | " | " | " |
| HO— | C₂H₅ | " | " | " | " | " |
| HO— | HS— | " | " | " | " | " |

TABLE IV-continued

| B | B₁ | R″₁ | R″₂ | R″₃ | R″₄ | R″₁₅ |
|---|---|---|---|---|---|---|
| HO— | CH₃S— | " | " | " | " | " |
| HO— | C₂H₅S— | " | " | " | " | " |
| HO— | HO— | " | ⌬CH₂OCH₂— | ⌬CH₂O— | H— | ⌬CH₂— |
| HO— | " | " | ⌬CH₂O— | " | " | " |
| HO— | " | " | CH₃O— | $\underset{\overset{\|}{CH_3C-O-}}{O}$ | " | $\underset{\overset{\|}{CH_3C-}}{O}$ |
| HO— | " | " | C₂H₅— | H | " | " |
| HO— | " | " | $\underset{\overset{\|}{CH_3C-OCH_2-}}{O}$ | $\underset{\overset{\|}{CH_3C-O-}}{O}$ | CH₃OCH₂— | " |
| HO— | " | " | " | " | C₂H₅— | " |
| HO— | " | CH₃OCH₂— | H | " | H | " |
| HO— | " | ⌬CH₂OCH₂— | " | " | " | ⌬CH₂— |
| HO— | " | " | $\underset{\overset{\|}{CH_3COCH_2-}}{O}$ | " | " | CH₃ |

PREPARATION 2c

N,N'-dicarbobenzyloxy-6'-acetoxy spectinomycin-3'-methylenol ether

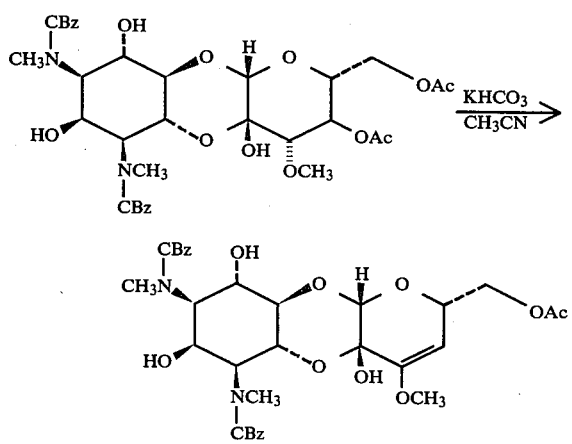

N,N'-dicarbobenzyloxy-3'-O-methyl-4'-(R)-6-diacetoxy-3'-(S)-dihydrospectinomycin, 101.3 mg (0.136 mmole) dissolved in 5.5 ml of acetonitrile is stirred with 350 mg of potassium bicarbonate 15 for 6 days at room temperature. The mixture is filtered through Celite ® and the bicarbonate is washed with more acetonitrile. Concentration of the filtrate gives 80.5 mg of N,N'-dicarbobenzyloxy 6'-acetoxy spectinomycin-3'-methylenol ether.

PMR (d₆-Acetone) 7.4 s, 5.1 s, 4.8 s, 4.75 s, 4.6–4 m, 3.9 s, 3.5 s, 2.0 s,

CMR (d₆-Acetone) 171.1, 158.0, 154.2, 138.2, 129.2, 128.5, 95.7, 95.5, 89.3, 75.3, 71.7, 67.4, 66.9, 66.5, 66.2, 6.08, 60.7, 57.8, 55.6, 30.8, 20.75 ppm.

Mass spec. (tri-trimethylsilyl derivative) m/e M+ = 888, M-15, 873.

Utilizing a procedure similar to Preparation 2c but substituting the appropriately-substituted hemiketals there are obtained the protected spectinomycin analogs of Tables V and VI.

TABLE V

[Structure: cyclohexane ring with N(CH₃)(CBz) and B at one carbon, B₁ and N(CH₃)(CBz) on opposite side, with O-linked sugar bearing R″₁, R″₂, R″₃, OR₁₆ substituents and OH]

| B | B₁ | R″₁ | R″₂ | R″₃ | R″₁₆ |
|---|---|---|---|---|---|
| HO— | HO— | H— | CH₃COCH₂— (CH₃C(O)CH₂—) | H | CH₃— |
| CH₃O— | HO— | " | " | " | " |
| C₂H₅O— | HO— | " | " | " | " |
| HS— | HO— | " | " | " | " |
| CH₃S— | HO— | " | " | " | " |
| C₂H₅S— | HO— | " | " | " | " |
| H— | HO— | " | " | " | " |
| HO— | H— | " | " | " | " |
| HO— | CH₃O— | " | " | " | " |
| HO— | C₂H₅— | " | " | " | " |
| HO— | HS— | " | " | " | " |
| HO— | CH₃S— | " | " | " | " |
| HO— | C₂H₅S— | " | " | " | " |
| HO— | HO— | " | C₆H₅CH₂OCH₂— | " | C₆H₅CH₂— |
| HO— | " | " | C₆H₅CH₂O— | " | " |
| HO— | " | " | CH₃O— | " | C₆H₅C(O)— |
| HO— | " | " | C₂H₅— | " | " |
| HO— | " | " | CH₃C(O)OCH₂— | CH₃— | " |
| HO— | " | " | " | CH₃CH₂— | " |
| HO— | " | C₆H₅C(O)OCH₂ | H | H— | " |
| HO— | " | " | " | " | C₆H₅CH₂— |
| HO— | " | " | " | " | CH₃— |

TABLE VI

[Structure: cyclohexane ring with N(CH₃)(CBz), B, B₁, N(CH₃)(CBz) substituents, S-linked sugar bearing R″₁, R″₂, R″₃, OR₁₆ substituents and OH]

| B | B₁ | R″₁ | R″₂ | R″₃ | R″₁₆ |
|---|---|---|---|---|---|
| HO— | HO— | H— | CH₃COCH₂— | H | CH₃— |
| CH₃O— | HO— | " | " | " | " |
| C₂H₅O— | HO— | " | " | " | " |
| HS— | HO— | " | " | " | " |

TABLE VI-continued

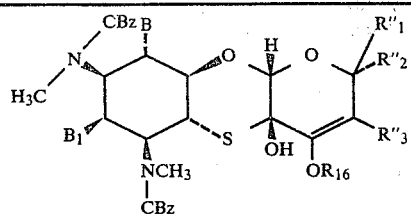

| B | B₁ | R"₁ | R"₂ | R"₃ | R"₁₆ |
|---|---|---|---|---|---|
| CH₃S— | HO— | " | " | " | " |
| C₂H₅S— | HO— | " | " | " | " |
| H— | HO— | " | " | " | " |
| HO— | H— | " | " | " | " |
| HO— | CH₃O— | " | " | " | " |
| HO— | C₂H₅— | " | " | " | " |
| HO— | HS— | " | " | " | " |
| HO— | CH₂S— | " | " | " | " |
| HO— | C₂H₅S— | " | " | " | " |
| HO— | HO— | " | ⌬—CH₂OCH₂— | " | ⌬—CH₂— |
| HO— | " | " | ⌬—CH₂O— | " | " |
| HO— | " | " | CH₃O— | " | ⌬—C(=O)— |
| HO— | " | " | C₂H₅— | " | " |
| HO— | " | " | CH₃C(=O)—OCH₂— | CH₃— | " |
| HO— | " | " | " | CH₃CH₂— | " |
| HO— | " | cyclohexyl-C(=O)—OCH₂— | H | H— | " |
| HO— | " | " | " | " | ⌬—CH₂— |
| HO— | " | " | " | " | CH₃ |

PREPARATION 3

N,N'-dicarbobenzyloxy-5'demethylspectinomycin

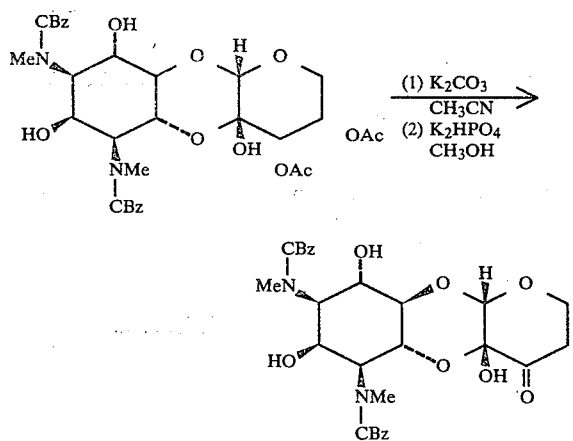

N,N'dicarbobenzyloxy-5-demethyl-3'-O-acetyl-4'-R-acetoxy-3'-(R)-dihydrospectinomycin (1.32 g, 1.92 mmol) is dissolved in 20 ml of acetonitrile and 1.00 g (7.24 mmol) of anhydrous potassium carbonate is added. After stirring 20 hours at room temperature, the mixture is filtered and the solid is washed with 20 ml more of acetonitrile. The solvent is removed in vacuo, 50 ml of methanol is added and the solution is treated with 1.40 g. (8.04 mmol) of dipotassium hydrogen phosphate. The mixture is stirred 22 hours at room temperature, filtered and the solid residue is washed well with methanol. Removal of solvent in vacuo gives 1.37 b of gummy orange solid. Rapid filtration through 40 g of silica gel (ethylacetate) gives 950 mg of white solid. Further purification on 2000 μ silica gel prep plates (ethylacetate) gives pure N,N'-dicarbobenzyloxy5'-demethylspectinomycin:

IR (CHCl₃) 3600, 3100, 1748, 1695, 1443, 1333, 1156, 1111, 700 cm⁻¹;

PMR (CDCl₃) δ 7.40 (s, 10, aromatic), 5.13 (s, 4), 3.1-5.0 (m), 3.05 and 2.95 (s', s, 6, NCH₃); CMR (d₆ acetone) (referenced to CD₃COCD₃) δ 201.5, 157.1.

156.8, 137.5, 128.5, 128.2, 127.8, 97.7, 92.4, 74.4, 74.1, 66.6, 65.8, 65.0, 60.8, 56.7, 38.2, 30.8.

Using procedures similar to that of Preparation 3 but substituting the appropriately substituted precursor hemiketal for N,N-biscarbobenzoxy-3'-O-acetyl-4'-(R)-acetoxydihydrospectinomycin, and respectively, there is obtained the protected spectinomycin analogs of Tables VII and VIII.

TABLE VII

| B | $B_1$ | $R''_1$ | $R''_2$ | $R''_3$ | $R''_4$ |
|---|---|---|---|---|---|
| HO— | HO— | H— | $CH_3COCH_2$— | H | H |
| $CH_3O$— | HO— | " | " | " | " |
| $C_2H_5O$— | HO— | " | " | " | " |
| HS— | HO— | " | " | " | " |
| $CH_3S$— | HO— | " | " | " | " |
| $C_2H_5S$— | HO— | " | " | " | " |
| H— | HO— | " | " | " | " |
| HO— | H— | " | " | " | " |
| HO— | $CH_3O$— | " | " | " | " |
| HO— | $C_2H_5$ | " | " | " | " |
| HO— | HS— | " | " | " | " |
| HO— | $CH_3S$— | " | " | " | " |
| HO— | $C_2H_5S$— | " | " | " | " |
| HO— | HO— | " | ⌬$CH_2OCH_2$— | ⌬$CH_2O$— | H— |
| HO— | " | " | ⌬$CH_2O$— | " | " |
| HO— | " | " | $CH_3O$— | H | " |
| HO— | " | " | $C_2H_5$— | H | " |
| HO— | " | $CH_3OCH_2$— | H | " | H |
| HO— | " | ⌬$CH_2OCH_2$— | " | " | " |
| HO— | " | $CH_3COCH_2$— | $CH_3COCH_2$— | $CH_3COCH_2$— | H |
| HO— | " | ⌬$CH_2OCH_2$— | ⌬$CH_2OCH_2$— | ⌬$CH_2OCH_2$— | H |
| HO— | " | $NH_2CH_2$— | H | H | H |

TABLE VIII

| B | $B_1$ | $R''_1$ | $R''_2$ | $R''_3$ | $R''_4$ |
|---|---|---|---|---|---|
| HO— | HO— | H— | $CH_3COCH_2$— | H | H |
| $CH_3O$— | HO— | " | " | " | " |
| $C_2H_5O$— | HO— | " | " | " | " |

TABLE VIII-continued

| B | B₁ | R″₁ | R″₂ | R″₃ | R″₄ |
|---|---|---|---|---|---|
| HS— | HO— | " | " | " | " |
| CH₃S— | HO— | " | " | " | " |
| C₂H₅S— | HO— | " | " | " | " |
| H— | HO— | " | " | " | " |
| HO— | H— | " | " | " | " |
| HO— | CH₃O— | " | " | " | " |
| HO— | C₂H₅ | " | " | " | " |
| HO— | HS— | " | " | " | " |
| HO— | CH₃S— | " | " | " | " |
| HO— | C₂H₅S— | " | " | " | " |
| HO— | HO— | " | C₆H₅CH₂OCH₂— | C₆H₅CH₂O— | H— |
| HO— | " | " | C₆H₅CH₂O— | | |
| HO— | " | " | CH₃O— | H | " |
| HO— | " | " | C₂H₅— | H | " |
| HO— | " | CH₃OCH₂— | H | " | H |
| HO— | " | C₆H₅CH₂OCH₂— | " | " | " |
| HO— | " | CH₃COCH₂— | CH₃COCH₂— | CH₃COCH₂— | H |
| HO— | " | C₆H₅CH₂OCH₂— | C₆H₅CH₂OCH₂— | C₆H₅CH₂OCH₂— | H |
| HO— | " | NH₂CH₂— | H | H | H |

PREPARATION 3a

N,N-dicarbobenzyloxy-6-hydroxy spectinomycin

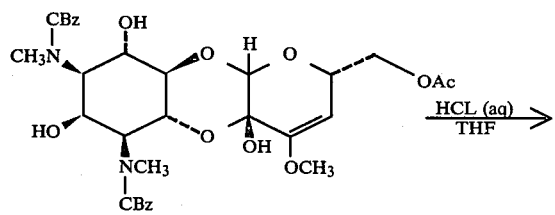

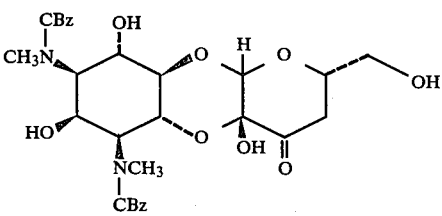

To a solution of N,N-dicarbobenzyloxy-6′-acetoxy spectinomycin-3′-methylenol ether (25 mg, 0.04 mmoles) in 0.65 ml of tetrahydrofuran is added 0.5 ml of 4 N aqueous hydrochloric acid. The solution is stirred for 28 hours at room temperature. The reaction is diluted with 25 ml of chloroform and washed with 4 ml of saturated sodium bicarbonate and water, respectively. The organic layer is collected, dried over sodium sulfate, filtered and concentrated to give 22 mg of N,N′-dicarbobenzyloxy-6′-hydroxy spectinomycin.

PMR (CDCl₃): 7.25 s, 5.1 s, 4.75 s, 4.5–3.5 m, 3.0, δs, CMR (CDCl₃) 157.5, 156.5, 136.3, 128.5, 128.1, 127.8, 96.8, 91.0, 77.0, 74.3, 74.0, 72.1, 67.6, 67.5, 65.8, 65.2, 64.4, 61.7, 57.1, 39.0, 29.7 ppm.

PREPARATION 3b

N,N-dicarbobenzyloxy-6-hydroxy spectinomycin

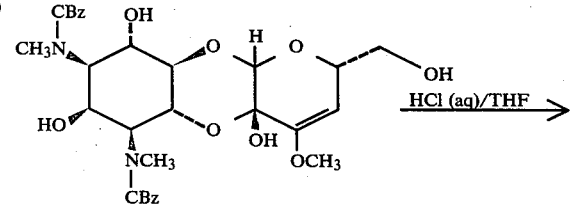

-continued

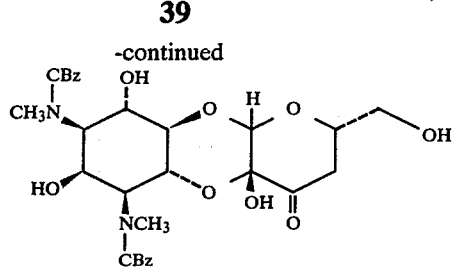

To a solution of N,N'-dicarbobenzyloxy-6-hydroxy-6-spectinomycin-3'-methylenol ether, 90 mg (0.143 mmoles) in 2.2 ml of tetrahydrofuran is added 1.6 ml of 4N aqueous hydrochloric acid. Reaction is stirred at room temperature for 24 hours and worked up as described in Preparation 3a. The N,N'-dicarbobenzyloxy-6-hydroxy spectinomycin displays the same TLC mobility and properties as the product of Preparation 3a. The products are combined and chromatographe on silica gel with 1:1 ETOAc:CHCl$_3$ elution system.

Utilizing procedures similar to those of Preparations 3a and 3b, but substituting the appropriately substituted δ enol ethers for δ enol ethers used in Preparations 3a and 3b there is obtained the protected analogs of spectinomycin of Tables IX and X.

TABLE IX

| B | B$_1$ | R$_1$ | R$_2$ | R$_3$ |
|---|---|---|---|---|
| HO— | HO— | H— | HOCH$_2$— | H |
| CH$_3$O— | HO— | " | " | " |
| C$_2$H$_5$O— | HO— | " | " | " |
| HS— | HO— | " | " | " |
| CH$_3$S— | HO— | " | " | " |
| C$_2$H$_5$S— | HO— | " | " | " |
| H— | HO— | " | " | " |
| HO— | H— | " | " | " |
| HO— | CH$_3$O— | " | " | " |
| HO— | C$_2$H$_5$— | " | " | " |
| HO— | HS— | " | " | " |
| HO— | CH$_3$S— | " | " | " |
| HO— | C$_2$H$_5$S— | " | " | " |
| HO— | HO— | " | ⌬CH$_2$OCH$_2$— | " |
| HO— | " | " | ⌬CH$_2$O— | " |
| HO— | " | " | CH$_3$O— | " |
| HO— | " | " | C$_2$H$_5$— | " |
| HO— | " | " | HOCH$_2$— | CH$_3$OCH$_2$ |
| HO— | " | " | " | C$_2$H$_5$ |
| HO— | " | CH$_2$OCH$_2$— | H | H |
| HO— | " | " | ⌬CH$_2$OCH$_2$— | " |

TABLE X

| B | B$_1$ | R$_1$ | R$_2$ | R$_3$ |
|---|---|---|---|---|
| HO— | HO— | H— | HOCH$_2$— | H |
| CH$_3$O— | HO— | " | " | " |
| C$_2$H$_5$O— | HO— | " | " | " |
| HS— | HO— | " | " | " |
| CH$_3$S— | HO— | " | " | " |
| C$_2$H$_5$S— | HO— | " | " | " |

TABLE X-continued

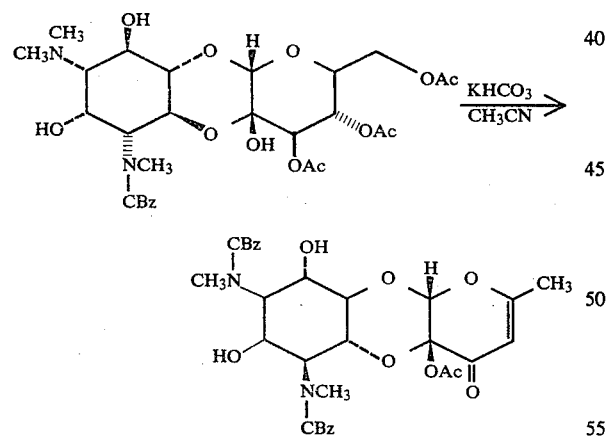

| B | B₁ | R₁ | R₂ | R₃ |
|---|---|---|---|---|
| H— | HO— | " | " | " |
| HO— | H— | " | " | " |
| HO— | CH₃O— | " | " | " |
| HO— | C₂H₅— | " | " | " |
| HO— | HS— | " | " | " |
| HO— | CH₃S— | " | " | " |
| HO— | C₂H₅S— | " | " | " |
| HO— | HO— | " | C₆H₅CH₂OCH₂— | " |
| HO— | " | " | C₆H₅CH₂O— | " |
| HO— | " | " | CH₃O— | " |
| HO— | " | " | C₂H₅— | " |
| HO— | " | " | HOCH₂— | CH₃OCH₂ |
| HO— | " | " | " | C₂H₅ |
| HO— | " | CH₃OCH₂— | H | H |
| HO— | " | C₆H₅CH₂OCH₂— | " | " |

PREPARATION 3c

N,N'-dicarbobenzyloxy-2'-O-acetyl-4',5'-didehydrospectinomycin

Anhydrous potassium bicarbonate (14.58 g, 146 meg) and acetonitrile (384 ml) are heated in a flask equipped with a distillation head. After 40 ml of solvent has been distilled, the remaining slurry is cooled to room temperature under nitrogen and then hemiketal triacetate of Preparation 2a is added. The mixture is stirred at room temperature for 41 hours by which time starting material is absent as judged by TLC (5 percent methanol in chloroform). The solid is filtered, washed and the filtrate concentrated. The residue is taken up in chloroform (40 ml) and inorganics filtered. The filtrate is concentrated to give a foam (14.51 g). After dissolving the foam in chloroform and cooling, a mass forms (7.55 g) which is recrystallized from chloroform (20 ml) to give 3.42 g of N,N'-dicarbobenzyloxy-2'-O-acetyl-4',5'-didehydrospectinomycin, mp 149°–152°. Chromatography of the combined mother liquors on silica gel (800 g) using 1:4 methanol-chloroform gives an additional 3.37 g of product (55 percent total yield).

UV (C₂H₅OH): 204.5 nm (20,950), 206 sh (20650), 267(11,550),

CD (CH₃OH) $[\theta]_{310}^{max}$ −22,000, $[\theta]_{266}^{max}$ +33,500, $[\alpha]_D^{27}$ −43° (C, 1 acetone).

PMR (CDCl₃): 2.07, (3H, s), 2.15 (3H, S), 3.08 (6H, s), 5.12 (4H), 5.40 (1H, s), 5.95 (1H, s), 7.32 (1OH, s).

CMR (CD₃COCD₃): 182.5, 172.9, 169.5, 137.6, 137.5, 128.6, 127.8, 102.7, 95.5, 93.1, 75.0, 74.0, 66.8, 65.6, 60.3, 59.6, 56.7, 31.1, 20.4 ppm.

Exact mass: 784.3097; required for C₃₈H₅₂N₂O₁₂ is 784.3059.

Using a procedure similar to that outlined in Preparation 3 but substituting the appropriately substituted hemiketal for the hemiketal prepared in Preparation 2a there is obtained the protected didehydrospectinomycin analogs of Tables XI and XII.

TABLE XI

| B | $B_1$ | $R_1$ | $R_{15}$ |
|---|---|---|---|
| HO— | HO— | $CH_3$— | $CH_3\overset{O}{\underset{\|}{C}}$— |
| $CH_3O$— | HO— | $CH_3$— | $CH_3\overset{O}{\underset{\|}{C}}$— |
| $C_2H_5O$— | HO— | $CH_3$— | $CH_3\overset{O}{\underset{\|}{C}}$— |
| HS— | HO— | $CH_3$— | $CH_3\overset{O}{\underset{\|}{C}}$— |
| $CH_3S$— | HO— | $CH_3$— | $CH_3\overset{O}{\underset{\|}{C}}$— |
| $C_2H_5S$— | HO— | $CH_3$— | $CH_3\overset{O}{\underset{\|}{C}}$— |
| H— | HO— | $CH_3$— | $CH_3\overset{O}{\underset{\|}{C}}$— |
| HO— | H— | $CH_3$— | $CH_3\overset{O}{\underset{\|}{C}}$— |
| HO— | $CH_3O$— | $CH_3$— | $CH_3\overset{O}{\underset{\|}{C}}$— |
| HO— | $C_2H_5$— | $CH_3$— | $CH_3\overset{O}{\underset{\|}{C}}$— |
| HO— | $H_2$— | $CH_3$— | $CH_3\overset{O}{\underset{\|}{C}}$— |
| HO— | $CH_3S$— | $CH_3$— | $CH_3\overset{O}{\underset{\|}{C}}$— |
| HO— | $C_2H_5S$— | $CH_3$— | $CH_3CH_2\overset{O}{\underset{\|}{C}}$— |
| HO— | HO— | $CH_3$— | $CH_3CH_2\overset{O}{\underset{\|}{C}}$— |
| HO— | HO— | $CH_3O$—$CH(CH_3)$— | $CH_3(CH_2)_2\overset{O}{\underset{\|}{C}}$— |
| HO— | HO— | $CH_3OCH_2$— | $CH_3(CH_2)_2\overset{O}{\underset{\|}{C}}$— |
| HO— | HO— | $C_2H_5$ | $CH_3(CH_2)_3\overset{O}{\underset{\|}{C}}$— |

TABLE XI-continued

| B | $B_1$ | $R_1$ | $R_{15}$ |
|---|---|---|---|
| HO— | HO— | $CH_3$— | $CH_3(CH_2)_3\overset{O}{\underset{\|}{C}}$— |
| HO— | HO— | $CH_3$— | isopropionyl |
| HO— | HO— | $C_3H_7$ | sec-butyryl |
| HO— | HO— | $C_3H_7$ | t-butyryl |

TABLE XII

| B | $B_1$ | $R_1$ | $R_{15}$ |
|---|---|---|---|
| HO— | HO— | $CH_3$— | $CH_3\overset{O}{\underset{\|}{C}}$— |
| $CH_3O$— | HO— | $CH_3$— | $CH_3\overset{O}{\underset{\|}{C}}$— |
| $C_2H_5O$— | HO— | $CH_3$— | $CH_3\overset{O}{\underset{\|}{C}}$— |
| HS— | HO— | $CH_3$— | $CH_3\overset{O}{\underset{\|}{C}}$— |
| $CH_3S$— | HO— | $CH_3$— | $CH_3\overset{O}{\underset{\|}{C}}$— |
| $C_2H_5S$— | HO— | $CH_3$— | $CH_3\overset{O}{\underset{\|}{C}}$— |
| H— | HO— | $CH_3$— | $CH_3\overset{O}{\underset{\|}{C}}$— |
| HO— | H— | $CH_3$— | $CH_3\overset{O}{\underset{\|}{C}}$— |
| HO— | $CH_3O$— | $CH_3$— | $CH_3\overset{O}{\underset{\|}{C}}$— |
| HO— | $C_2H_5$— | $CH_3$— | $CH_3\overset{O}{\underset{\|}{C}}$— |
| HO— | $H_2$— | $CH_3$— | $CH_3\overset{O}{\underset{\|}{C}}$— |

TABLE XII-continued

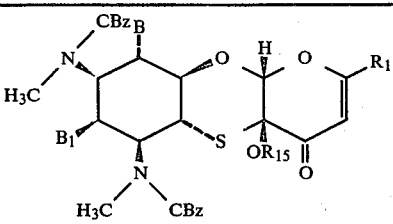

| B | B₁ | R₁ | R₁₅ |
|---|---|---|---|
| HO— | CH₃S— | CH₃— | $\underset{\parallel\ \ \ }{\overset{O}{CH_3C-}}$ |
| HO— | C₂H₅S— | CH₃— | $\underset{\parallel\ \ \ \ \ \ \ }{\overset{O}{CH_2CH_2C-}}$ |
| HO— | HO— | CH₃— | $\underset{\parallel\ \ \ \ \ \ \ }{\overset{O}{CH_2CH_2C-}}$ |
| HO— | HO— | CH₃O—CH(CH₃)— | $\underset{\parallel\ \ \ \ \ \ \ }{\overset{O}{CH_3(CH_2)_2C-}}$ |
| HO— | HO— | CH₃OCH₂— | $\underset{\parallel\ \ \ \ \ \ \ }{\overset{O}{CH_3(CH_2)_2C-}}$ |
| HO— | HO— | C₂H₅— | $\underset{\parallel\ \ \ \ \ \ \ }{\overset{O}{CH_3(CH_2)_3C-}}$ |
| HO— | HO— | CH₃— | $\underset{\parallel\ \ \ \ \ \ \ }{\overset{O}{CH_3(CH_2)_3-C}}$ |
| HO— | HO— | CH₃ | isopropionyl |
| HO— | HO— | C₃H₇ | sec-butyryl |
| HO— | HO— | C₃H₇ | t-butyryl |

PREPARATION 4

N,N′-biscarbobenzyloxy-4′,5′-didehydrospectinomycin

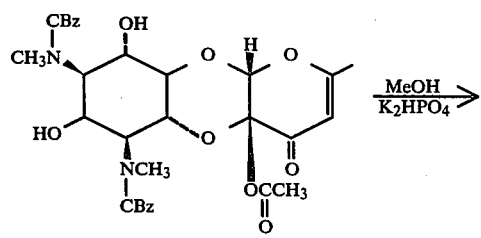

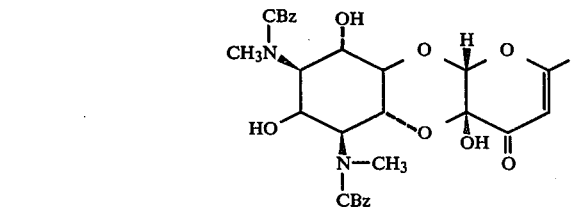

N,N′-biscarbobenzyloxy-2′-O-acetyl-4,5′-didehydrospectinomycin (1.0 g) is added to a slurry of dipotassium hydrogen phosphate (0.40 g) in anhydrous methanol (20 ml) and stirred at room temperature for 1½ hours. The solvent is removed at reduced pressure and the organics dissolved in 1½ percent methanol in chloroform and chromatographed on silica gel (225 g) using 1½ percent methanol in chloroform. The product contain- ing fractions are combined and concentrated to yield 0.51 g (55 percent) of N,N′-biscarbobenzyloxy-4′,5′-didehydrospectinomycin.

CD (CH₃OH): $[\theta]_{314}^{max}$ −8,300±2,100, $[\theta]_{266}^{max}$+10,500±2,100 $[\alpha]_D$−56° (C 1.0, CH₃OH)

CMR(CD₃COCD₃): 187.6, 175.8, 157.2, 138.1, 128.4, 101.7, 99.3, 87.7, 76.3, 64.6, 63.8, 67.3, 66.7, 66.3, 65.3, 60.8, 60.0, 31.5, 21.3 ppm.

Mass spectrum: m/e (triTMS); 814 (M+), 799 (M-15).

Utilizing a procedure similar to that used in Preparation 4, but substituting the appropriately substituted didehydrospectinomycin derivative for N,N′-biscarbobenzyloxy-2′-O-acetyl-4′,5′-didehydrospectinomycin there is obtained the protected didehydrospectinomycin analogs of Tables XIII and XIV.

TABLE XIII

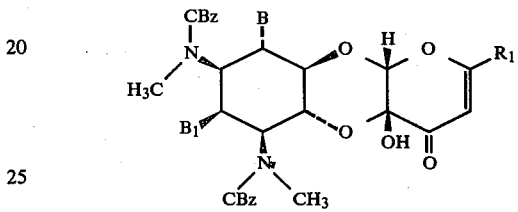

| B | B₁ | R₁ |
|---|---|---|
| HO— | HO— | CH₃— |
| CH₃O— | HO— | CH₃— |
| C₂H₅O— | HO— | CH₃— |
| HS— | HO— | CH₃— |
| CH₃S— | HO— | CH₃— |
| C₂H₅S— | HO— | CH₃— |
| H— | HO— | CH₃— |
| HO— | H— | CH₃— |
| HO— | CH₃O— | CH₃— |
| HO— | C₂H₅— | CH₃— |
| HO— | H₂— | CH₃— |
| HO— | CH₃S— | CH₃— |
| HO— | C₂H₅S— | CH₃ |
| HO— | HO— | CH₃— |
| HO— | HO— | CH₃— |
| HO— | HO— | CH₂OCH₂— |
| HO— | HO— | C₂H₅ |
| HO— | HO— | CH₃— |
| HO— | HO— | CH₃— |
| HO— | HO— | C₂H₇ |

TABLE XIV

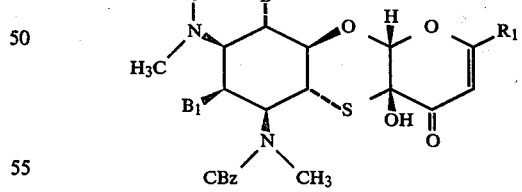

| B | B₁ | R₁ |
|---|---|---|
| HO— | HO— | CH₃— |
| CH₃O— | HO— | CH₃— |
| C₂H₅O— | HO— | CH₃— |
| HS— | HO— | CH₃— |
| CH₃S— | HO— | CH₃— |
| C₂H₅S— | HO— | CH₃— |
| H— | HO— | CH₃— |
| HO— | H— | CH₃— |
| HO— | CH₃O— | CH₃— |
| HO— | C₂H₅— | CH₃— |
| HO— | H₂— | CH₃— |
| HO— | CH₃S— | CH₃— |
| HO— | C₂H₅S— | CH₃— |

TABLE XIV-continued

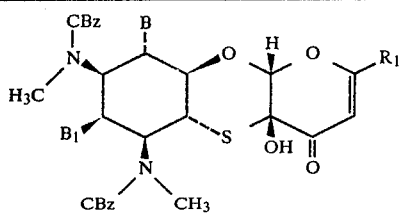

| B | B₁ | R₁ |
|---|---|---|
| HO— | HO— | CH₃— |
| HO— | HO— | CH₃— |
| HO— | HO— | CH₃OCH₂— |
| HO— | HO— | C₂H₅ |
| HO— | HO— | CH₃ |
| HO— | HO— | CH₃ |
| HO— | HO— | C₃H₇ |

PREPARATION 5

N,N'-dicarbobenzyloxy-6'-hydroxy-spectinomycin-3'-methylenol

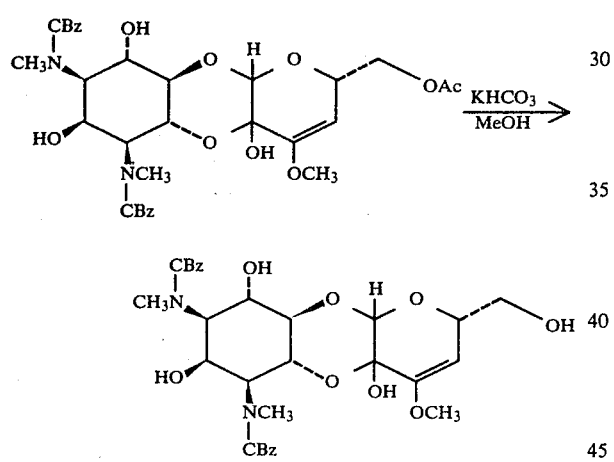

The enol ether N,N'-dicarbobenzyl-5'-acetoxy-spectinomycin, 3'-methylenol ether, 103.9 mg (0.154 mmoles) dissolved in 6.8 ml of methanol is stirred with potassium bicarbonate (115 mg) for 24 hours at room temperature. The mixture is concentrated, redissolved in chloroform, filtered and concentrated again to give 90 mg of N,N'-dicarbobenzyloxy-6'hydroxy-spectinomycin, 3'-methylenol ether. No acetate methyl observed in PMR or CMR.

PMM (CDCl₃) 7.31 s, 5.10 s, 5–3.75 m, 3.5 s, 3.1 δ s.

CMR (CDCl₃) 158, 152.5, 136.5, 128.2, 95.1, 94.9, 88.7, 77.2, 67.5, 67.2, 55.0, 34.1, 29.72 ppm Mass Spec. (tetra-trimethylsilyl derivative) m/e (M+) 918 (M-15) 903

Utilizing a procedure similar to that of Preparation 5 but substituting the appropriately substituted enol ethers there is obtained the protected spectinomycin analogs of Tables XV and XVI.

TABLE XV

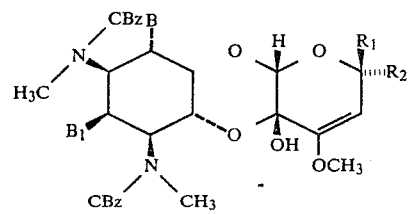

| B | B₁ | R₁ | R₂ |
|---|---|---|---|
| HO— | HO— | H— | HOCH₂— |
| CH₃O— | HO— | " | " |
| C₂H₅O— | HO— | " | " |
| HS— | HO— | " | " |
| CH₃S— | HO— | " | " |
| C₂H₅S— | HO— | " | " |
| H— | HO— | " | " |
| HO— | H— | " | " |
| HO— | CH₃O— | " | " |
| HO— | C₂H₅— | " | " |
| HO— | HS— | " | " |
| HO— | CH₃S— | " | " |
| HO— | C₂H₅S— | " | " |

TABLE XVI

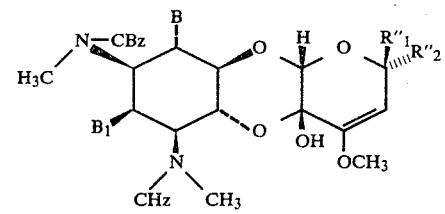

| B | B₁ | R''₁ | R''₂ |
|---|---|---|---|
| HO— | HO— | H— | HOCH₂— |
| CH₃O— | HO— | " | " |
| C₂H₅O— | HO— | " | " |
| HS— | HO— | " | " |
| CH₃S— | HO— | " | " |
| C₂H₅S— | HO— | " | " |
| H— | HO— | " | " |
| HO— | H— | " | " |
| HO— | CH₃O— | " | " |
| HO— | C₂H₅— | " | " |
| HO— | HS— | " | " |
| HO— | CH₃S— | " | " |
| HO— | C₂H₅S— | " | " |

PREPARATION 6

N,N'-dicarbobenzyloxy-6'-chlorospectinomycin

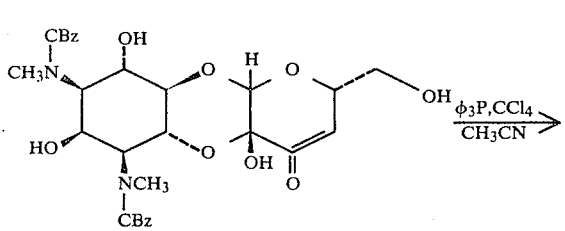

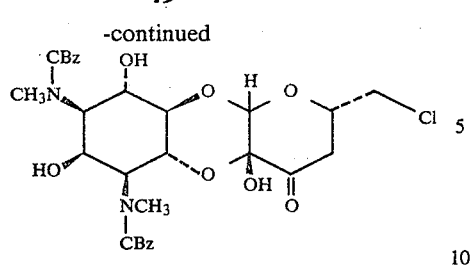

A solution of N,N'-dicarbobenzyloxy-6'-hydroxyspectinomycin (200 mg, 0.32 mMol) and triphenylphosphine (170 mg, 0.65 mMol) in carbon tetrachloride (10 mL) and acetonitrile (5 mL) is stirred at room temperature for 24 hrs. An additional 80 mg of triphenylphosphine is added and stirring is continued for another 24 hrs. The reaction is concentrated to an oil, redissolved in chloroform (50 mL) and washed with 0.1 hydrochloric acid (15 mL) and saturated sodium bicarbonate (30 mL). The aqueous phase is extracted with chloroform and the organic phases are combined, dried over sodium sulfate, and concentrated. The crude product is chromatographed on three 1000 micron silica gel preparative TLC plates in 1:9 methanol:chloroform. The silica gel is washed with warm ethyl acetate and filtered. The filtrate is concentrated, redissolved in chloroform, filtered through Celite ®, and concentrated to give 87.9 mg, (42%) of N,N'-dicarbobenzyloxy-6'-chlorospectinomycin.

CMR (d$_6$-acetone): 192 (C-3' carbonyl, folded), 157, 138.0, 129.2, 128.4, 97.3, 92.1, 75.2, 74.7, 71.5, 67.3, 66.4, 65.7, 60.2, 60.9, 57.4, 47.0, 41.6, 31.5 ppm.

Mass spectrum: (triTMS); 850 (M+), 835, 822, 814, 745, 629.

PREPARATION 7

N,N'-dicarbobenzyloxy-6'-bromospectinomycin

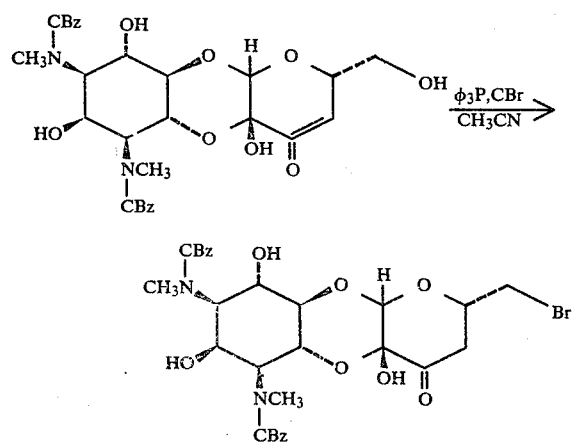

A solution of N,N'-dicarbobenzyloxy-6'-hydroxyspectinomycin (250 mg, 0.406 mMol), triphenylphosphine (270 mg, 1.03 mMol), and carbon tetrabromide (1 g, 3.02 mMol) in acetonitrile (4 mL) is stirred at room temperature for 2.5 days. The reaction is then concentrated and chromatographed on two 1500 micron silica gel preparative TLC plates in ethyl acetate. The silica is washed with warm acetonitrile and filtered. The filtrate is concentrated to give 105 mg (37%) of N,N'-dicarbobenzyloxy-6'-bromospectinomycin.

CMR (d$_6$-acetone): 192 (C-3' folded), 157, 138.1, 129.2, 128.4, 97.2, 92.0, 75.2, 74.5, 70.9, 67.3, 66.3, 65.6, 60.5, 57.5, 42.5, 35.5, 31.5 ppm.

Mass spectrum: (triTMS); 896 894 (M+), 881 879 (M-15), 814 (M-HBr), 745, 629.

PREPARATION 8

N,N'-dicarbobenzyloxy-6'-acetoxyspectinomycin

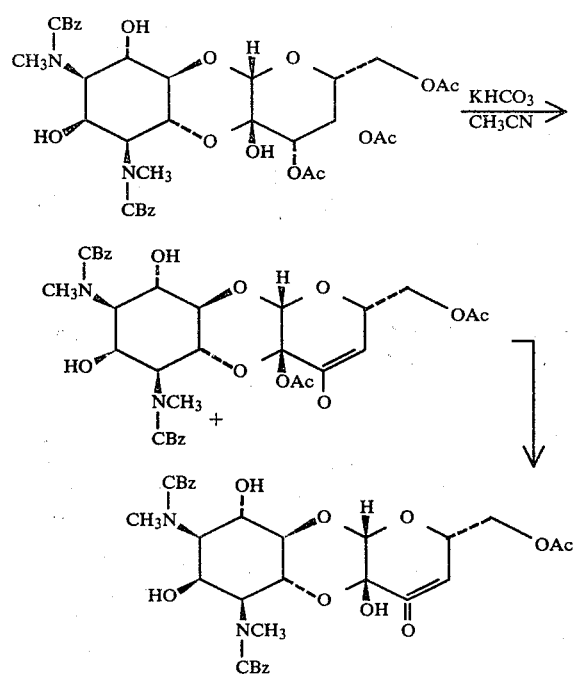

A solution of the triacetate N,N'-dicarbobenzyloxy-3'-0-acetyl-4' (R)-acetoxy-6'acetoxy-3'(S)-dihydrospectinomycin (150 mg, 0.197 mMol) in acetonitrile (5.25 ml) is stirred with potassium bicarbonate (450 mg) for 22 hrs. TLC analysis of the reaction in 5:95 methanol-methylene chloride shows a complete reaction and two major products with Pf values of 0.6 and 0.3. The reaction mixture is filtered and concentrated to give 119 mg of the crude products. CMR analysis of the crude products shows that they exhibit very similar spectra with substantial differences only in the anomeric region of C-1', 2', and C-3'. The spectra are totally consistent with the two mono-eliminated products N,N'-dicarbobenzyloxy-6'-acetoxy-2'-0-acetylspectinomycin and N,N'-dicarbobenzyloxy-6'acetoxyspectinomycin. The crude product is chromatographed on 20 g of silica gel using 1:1 ethyl acetate chloroform, to yield 75.8 mg of N,N'-dicarbobenzyloxy-6'-acetoxyspectinomycin. This material is charaterized by CMR and mass spectrum and has a structure of N,n'-dicarbobenzyloxy-6'-acetoxyspectinomycin.

Crude Product Mixture:

CMR (d$_6$-acetone): 195.8, 191.8, 171.1, 170.0, 157, 138.0, 129.2, 128.4, 97.4, 95.7, 94.8, 92.3, 75.1, 74.6, 74.4 74.4, 73.8, 70.0, 69.8, 67.3, 66.11, 65.8, 60.4, 57.3, 40.9, 40.6, 31.4, 20.8, 20.6 ppm.

N,N'-dicarbobenzyloxy-6'-acetoxyspectinomycin:

CMR (d$_6$-acetone): 191.8, 171.0, 157, 138.0, 129.2, 128.5, 97.4, 92.3, 75.1, 74.0, 70.0, 67.3, 66.4, 66.1, 65.7, 60.3, 57.4, 40.6, 31.5, 20.6 ppm.

Mass spectrum: (triTMS); 874 (M+), 859, 745, 629.

PREPARATION 9

N,N'-dicarbobenzyloxy-6'-hydroxyspectinomycin

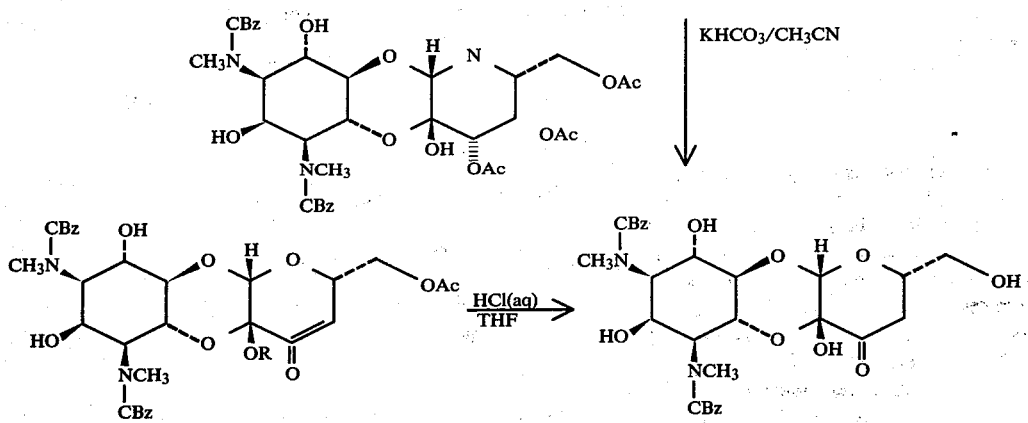

A solution of N,N'-dicarbobenzyloxy-3'-0-acetyl-4'-(R)-acetoxy-6'-acetoxy-3'(5)-dihydrospectinomycin (490 mg, 0.64 mMole) in acetonitrile is stirred with potassium bicarbonate (1.5 g) for 48 hours. The reaction is filtered and concentrated to give 460 mg of crude products. Theproduct redissolved in tetrahydrofuran (bml) and 4N hydrochloric acid (3 ml). The reaction is stirred for 24 hrs at 25° C. Work up of the reaction involves dilution with chloroform (200 ml) followed by washes of the organic layer with saturated bicarbonate solution and water. The organic layer is dried over sodium sulfate and concentrated to give 330 mg of product. TLC and CMR showed the product to be at least 84–90% pure. The product was identified by CMR, mass spec., HC to be N,N'-dicarbobenzyloxy-6'-hydroxyspectinomycin.

EXAMPLE 1

Spectinomycin

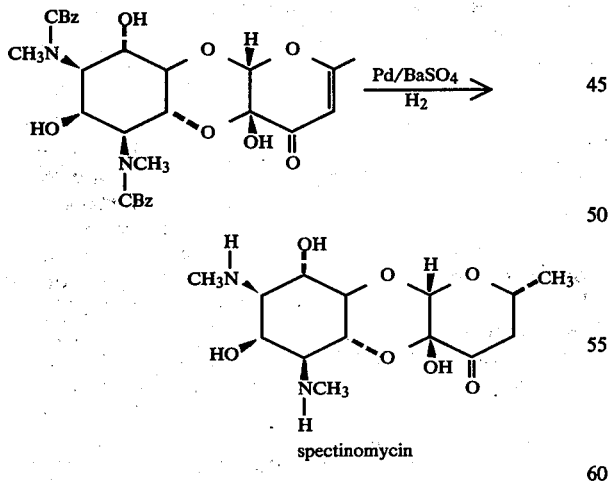

To a solution of 480 mg (0.80 mmol) of N,N'-biscarbobenzyloxy-4',5'-didehydrospectinomycin in 40 ml of isopropyl alcohol is added 480 mg of 10 percent palladium on barium sulfate and 0.48 ml (5.9 mmol) of pyridine. The mixture is hydrogenated at atmospheric pressure for 5 hours, filtered and the filtrate concentrated in vacuo. The residue is redissolved in isopropyl alcohol and treated with 2.0 ml (2.0 mmol) of a 1 N solution of hydrogen chloride in isopropyl alcohol. Removal of solvent in vacuo gives 440 mg of white solid. Recrystallization from aqueous acetone gives 164 mg (0.33 mmol, 41 percent) of spectinomycin dihydrochloride pentahydrate having the same physical and biological properties as the natural product.

By applying the same procedure to the enoneacetate prepared in Preparation 3c, a 35 percent yield of crystalline spectinomycin dihydrochloride pentahydrate is obtained.

EXAMPLE 2

5-Desmethylspectinomycin

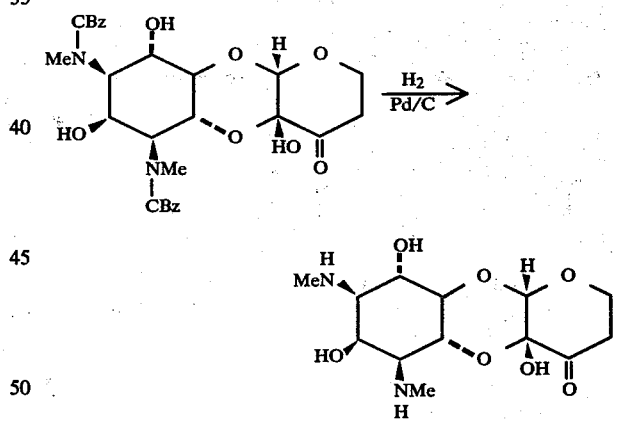

A solution of 333 mg (0.57 mmol) of N,N'-dicarbobenzyloxy- 5'-desmethylspectinomycin in 5 ml of isopropyl alcohol is added to 300 mg of 10 percent Pd on carbon in 45 ml of isopropyl alcohol in a Parr bottle. The solution is treated with 1.36 ml (1.36 mmol) of 1 N hydrogen chloride in isopropyl alcohol and hydrogenated 16 hours at 40 psi at room temperature. The material is filtered and the catalyst is washed with isopropyl alcohol. Washing the catalyst further with water removes more product. The material is concentrated in vacuo to dryness and the water soluble portion is separated. Removal of solvent in vacuo gives a white residue which recrystallizes from aqueous acetone to give 112 mg of 5'-desmethylspectinomycin as a white solid: mp 196°–205° decomp.; MS m/e (penta TMS derivative) 678.3378; required for $C_{28}H_{62}N_2O_7Si_5$ 678.3403;

CMR (D₃O) (refers to external TMS) δ95.3, 94.9, 93.6, 71.1, 67.4, 67.0, 62.9, 62.5, 6T.0, 59.9, 35.9, 32.2, 31.7.

EXAMPLE 3

6'-Hydroxyspectinomycin

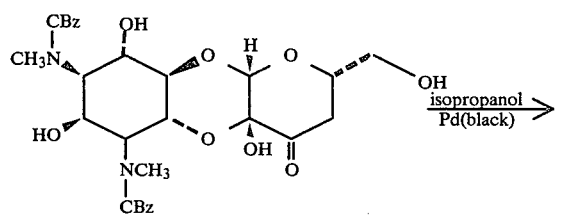

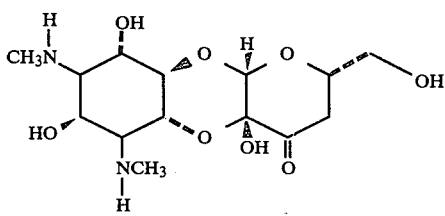

36 mg of N,N'-dicarbobenzyloxy-6-hydroxy spectinomycin is shaken with 20 mg of palladium black in 35 ml of isopropanol under 4 pounds of hydrogen pressure for 2.25 hours. The catalyst is filtered and washed with isopropyl alcohol. The filtrate is concentrated to 10 ml total volume and to it is added 0.12 ml of 1.0 N hydrochloric acid in isopropyl alcohol. Concentration of the solution gives a white residue which is redissolved in D₂O. for ¹³C. Recovery of the ¹³C sample gives 14 mg of material after lyophilization. This material is crystallized from water and acetone to yield 6'-hydroxy spectinomycin.

mp 201°–205° (dec.).

CMR (D₂O) 94.9, 93.2, 73.6, 70.7, 67.2, 64.6, 62.7, 60.8, 59.6, 37.0, 31.9, 31.4 ppm spectinomycin Rf. 0.5

6'-hydroxyspectinomycin Rf. 0.25

Dipped disk assay of crude product 6'-hydroxyspectinomycin shows antibacterial activity.

Utilizing procedures similar to that of Examples 1–6, but substituting the appropriately substituted protected spectinomycin for N,N'-biscarbobenzyloxy-4', 5'-didehydrospectinomycin and N,N'-dicarbobenzyloxy-5'desmethylspectinomycin, N,n'-dicarbobenzyloxy-6'-hydrospectinomycin, N,N'-dicarbobenzyloxy-6'-chlorospectinomycin, N,N'-dicarbobenzyloxy-6'-bromospectinomycin, and N,N'-dicarbobenzyloxy-6'-acetoxyspectinomycin, there is obtained analogs of spectinomycin set forth in Tables XVII and XVIII.

EXAMPLE 4

6'-Chlorospectinomycin and its dihydrochloride

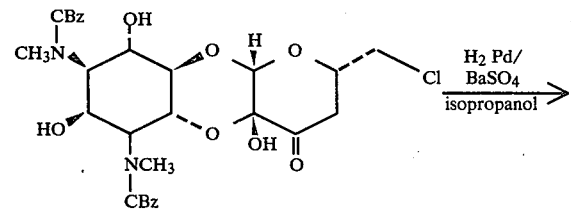

-continued

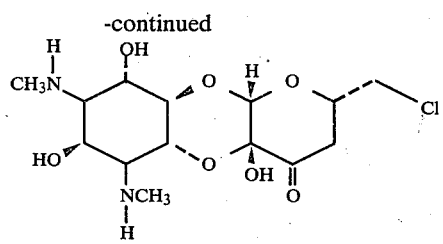

To a solution of N,N'-dicarbobenzyloxy-6'-chlorospectinomycin (43.4 mg), 0.068 mMol) in isopropanol (5.5 mL) is added 42 mg of 10% palladium on barium sulfate. The reaction flask is purged with vacuum/nitrogen cycles then with vacuum/hydrogen cycles. The mixture is stirred under hydrogen at atmospheric pressure for 1 hr. The reaction is dilution with isopropanol (25 mL) and filtered through Celite. The filtrate is concentrated to approximately 10 mL, acidified with hydrochloric acid in isopropanol, and concentrated to a solid. This solid is dissolved with water (4mL), filtered and lyophilized to give 30 mg of crude product. The crude product is precipitated from water and acetone to give 7 mg (23.5%) of pure 6'-chlorospectinomycin dihydrochloride.

CMR (D₂O): 94.7, 94.5, 92.9, 72.3, 71.0, 67.0, 66.8, 62.7, 60.7, 59.8, 47.5, 38.3, 31.9, 31.4.

Mass spectrum: (triTMS); 581 (M-1), 566, 551, 545 (M-1)-HCl.

EXAMPLE 5

6'-Bromospectinomycin and its dihydrochloride

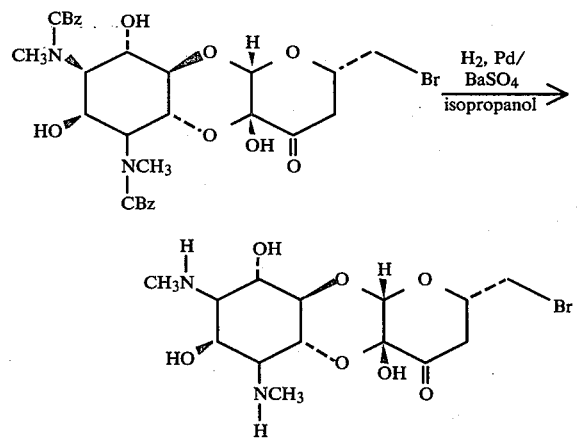

To a solution of N,N'-dicarbobenzyloxy-6'-bromospectinomycin (29.9 mg, 0.044 mMol) in isopropanol (3.0 mL) is added 50 mg of 10% palladium on barium sulfate. The reaction is stirred under hydrogen at atmospheric pressure for 3 hrs. The reaction rate slows so the catalyst is filtered, and the reaction restarted with 65 mg of new catalyst, followed by an additional 70 mg of fresh catalyst after 2 hrs. the reaction is stirred one more hour and then filtered through Celite. The filtrate is concentrated to one third its volume and acidified with 1N hydrochloric acid in isopropanol (0.15 mL) and concentrated to solid. The crude solid is redissolved in water (3 mL), filtered, and lyophilized to give 17 mg (79%) of 6'-bromospectinomycin.

CMR (D₂O): 94.7, 94.6, 92.8, 71.6, 71.0, 67.1, 66.8, 62.8, 60.8, 59.8, 39.3, 36.3, 31.9, 31.5 ppm.

EXAMPLE 6

6'-Acetoxyspectinomycin

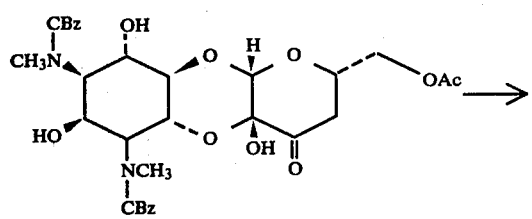 → 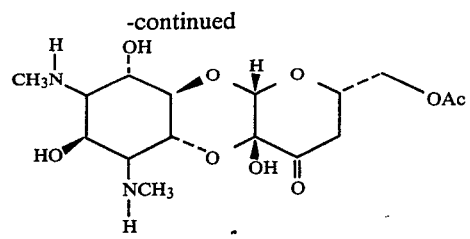

To solution of 100 mg of N,N'-dicarbobenzyloxy-6'-acetoxyspectinomycin in in 5 mL of isopropyl alcohol is added 100 mg of 10% palladium on barium sulfate. The mixture is stirred under hydrogen for 4 hrs. The catalyst is removed by filtration and the filtrate concentrated to give 0'-acetoxyspectinomycin.

TABLE XVII

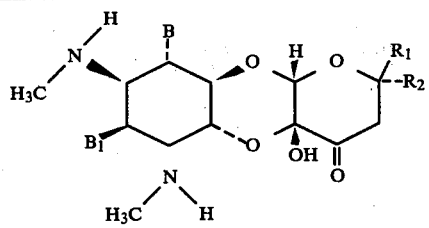

| B | $B_1$ | $R_1$ | $R_2$ | $R_3$ | $R_4$ |
|---|---|---|---|---|---|
| HO— | HO— | H— | $HOCH_2$— | H— | H— |
| $CH_3O$— | HO— | H— | $HOCH_2$— | H— | H— |
| $C_2H_5O$— | HO— | H— | $HOCH_2$— | H— | H— |
| HS— | HO— | H— | $HOCH_2$— | H— | H— |
| $CH_3S$— | HO— | H— | $HOCH_2$— | H— | H— |
| $C_2H_5S$— | HO— | H— | $HOCH_2$— | H— | H— |
| H— | HO— | H— | $HOCH_2$— | H— | H— |
| HO— | H— | H— | $HOCH_2$— | H— | H— |
| HO— | $CH_3O$— | H— | $HOCH_2$— | H— | H— |
| HO— | $C_2H_5$— | H— | $HOCH_2$— | H— | H— |
| HO— | H— | H— | $HOCH_2$— | H— | H— |
| HO— | $CH_3S$— | H— | $HOCH_2$— | H— | H— |
| HO— | $C_2H_5S$— | H— | $HOCH_2$— | H— | H— |
| HO— | HO— | H— | $HOCH_2$— | H— | H— |
| HO— | HO— | H— | $C_2H_5$ | H— | H— |
| HO— | HO— | H— | $HOCH_2$— | H— | H— |
| HO— | HO— | H— | $CH_3OCH_2$— | H— | H— |
| HO— | HO— | $HOCH_2$— | H— | H— | H— |
| HO— | HO— | H— | $CH_3$— | H— | H— |
| HO— | HO— | H— | $CH_3$— | H— | H— |
| HO— | HO— | H— | $CH_3$— | H— | H— |
| HO— | HO— | $CH_3\overset{O}{\overset{\|}{C}}OCH_2$ | $CH_3\overset{O}{\overset{\|}{C}}OCH_2$ | $CH_3\overset{O}{\overset{\|}{C}}OCH_2$— | H— |
| HO— | HO— | ⌬$CH_2OCH_2$ | ⌬$CH_2OCH_2$ | ⌬$CH_2OCH_2$ | H— |
| HO— | HO— | $NH_2CH_2$— | H— | H— | H— |

TABLE XVIII

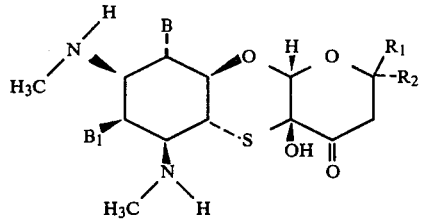

| B | $B_1$ | $R_1$ | $R_2$ | $R_3$ | $R_4$ |
|---|---|---|---|---|---|
| HO— | HO— | H— | $HOCH_2$— | H— | H— |
| $CH_3O$— | HO— | H— | $HOCH_2$— | H— | H— |
| $C_2H_5O$— | HO— | H— | $HOCH_2$— | H— | H— |
| HS— | HO— | H— | $HOCH_2$— | H— | H— |
| $CH_3S$— | HO— | H— | $HOCH_2$— | H— | H— |
| $C_2H_5S$— | HO— | H— | $HOCH_2$— | H— | H— |
| H— | HO— | H— | $HOCH_2$— | H— | H— |
| HO— | H— | H— | $HOCH_2$— | H— | H— |
| HO— | $CH_3O$— | H— | $HOCH_2$— | H— | H— |
| HO— | $C_2H_5$— | H— | $HOCH_2$— | H— | H— |
| HO— | H— | H— | $HOCH_2$— | H— | H— |
| HO— | $CH_3S$— | H— | $HOCH_2$— | H— | H— |
| HO— | $C_2H_5S$— | H— | $HOCH_2$— | H— | H— |
| HO— | HO— | H— | $HOCH_2$— | H— | H— |
| HO— | HO— | H— | $C_2H_5$ | H— | H— |
| HO— | HO— | H— | $HOCH_2$— | H— | H— |
| HO— | HO— | H— | $HOCH_2$— | H— | H— |
| HO— | HO— | $CH_3OCH_2$— | H— | H— | H— |
| HO— | HO— | $HOCH_2$— | H— | H— | H— |
| HO— | HO— | H— | $CH_3$— | H— | H— |
| HO— | HO— | H— | $CH_3$— | H— | H— |
| HO— | HO— | H— | $CH_3$— | H— | H— |
| HO— | HO— | $CH_3\overset{O}{\overset{\|}{C}}OCH_2$ | $CH_3\overset{O}{\overset{\|}{C}}OCH_2$ | $CH_3\overset{O}{\overset{\|}{C}}OCH_2$— | H— |
| HO— | HO— | $\langle\bigcirc\rangle CH_2OCH_2$ | $\langle\bigcirc\rangle CH_2OCH_2$ | $\langle\bigcirc\rangle CH_2OCH_2$ | H— |
| HO— | HO— | $NH_2CH_2$— | H— | H— | H— |

EXAMPLE 7

4', 5'-Didehydrospectinomycin dihydrochloride

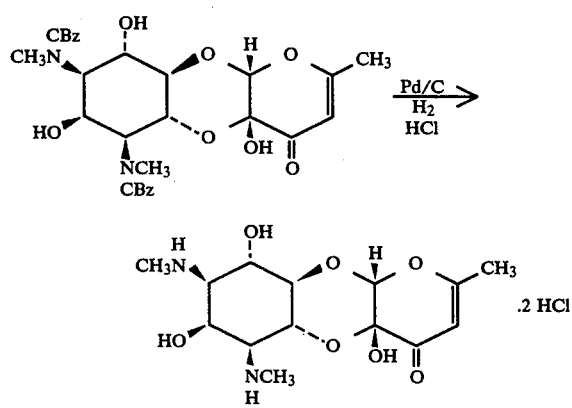

A mixture containing N,N'-biscarbobenzyloxy-4',5'-didehydrospectinomycin (93 mg), 10 percent palladium on carbon (70 mg), isopropyl alcohol (30 ml) and 0.1 N HCl is isopropyl alcohol (2 ml) is hydrogenated at 30 psi for 1 ½ hours. At this point, more catalyst (30 mg) and 0.1 N HCl in isopropyl alcohol (1.0 ml) is added and the hydrogenation is resumed for 2 ½ hours. The solid is then filtered and the filtrate concentrated to give 50 mg of 4',5'-didehydrospectinomycin dihydrochloride as a solid. This product is active against *E. coli* and did not contain spectinomycin or dihydrospectinomycin as shown in several TLC systems ($CHCl_3$:$CH_3OH$:$NH_4OH$-3:4:2) (3 percent $NH_4OH$ acetone). In this system it shows a $\mu\nu$ active spot which corresponded to a reference standard of enantiomeric 4',5'-dehydrospectinomycin which is characterized as follows:

Mass spectrum (tri-TMS): m/e 546 (M+), 531 (H-15), 492, 426, 401, 361, 271, 199.

CMR ($D_2O$, external TMS): 189.6, 179.3, 102.8, 98.5, 72.6, 69.9, 67.0, 66.5, 62.6, 61.5, 59.7, 32. 32.1, 22.0 ppm.

Utilizing a procedure similar to that of Example 7, but substituting the appropriately substituted 4',5'-didehydrospectinomycin for N,N'-biscarbobenzyloxy 4',5'-didehydrospectinomycin there is obtained the 4',5'-didehydrospectinomycins of Tables XIX and XX.

TABLE XIX

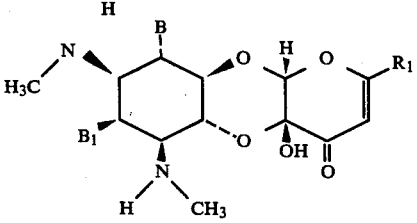

| B | $B_1$ | $R_1$ |
|---|---|---|
| HO— | HO— | $CH_3$— |

TABLE XIX-continued

[Structure diagram showing compound with H3C-N(H)- group, B, B1, O, OH, R1 substituents and N(H)(CH3) group]

| B | B₁ | R₁ |
|---|---|---|
| CH₃O— | HO— | CH₃— |
| C₂H₅O— | HO— | CH₃— |
| HS— | HO— | CH₃— |
| CH₃S— | HO— | CH₃— |
| C₂H₅S— | HO— | CH₃— |
| H— | HO— | CH₃— |
| HO— | H— | CH₃— |
| HO— | CH₃O— | CH₃— |
| HO— | C₂H₅— | CH₃— |
| HO— | H₂— | CH₃— |
| HO— | CH₃S— | CH₃— |
| HO— | C₂H₅S— | CH₃— |
| HO— | HO— | CH₃— |
| HO— | HO— | C₂H₅— |
| HO— | HO— | HOCH₂— |
| HO— | HO— | HOCH₂— |
| HO— | HO— | C₃H₇— |
| HO— | HO— | C₃H₃ |
| HO— | HO— | ClCH₂— |
| HO— | HO— | ClCH₂CH₂— |
| HO— | HO— | BrCH₂— |
| HO— | HO— | BrCH₂CH₂— |
| HO— | HO— | NH₂CH₂— |
| HO— | HO— | CH₃COCH₂— (with C=O) |

TABLE XX

[Structure diagram similar to above but with S substituent]

| B | B₁ | R₁ |
|---|---|---|
| HO— | HO— | CH₃— |
| CH₃O— | HO— | CH₃— |
| C₂H₅O— | HO— | CH₃— |
| HS— | HO— | CH₃— |
| CH₃S— | HO— | CH₃— |

TABLE XX-continued

[Structure diagram]

| B | B₁ | R₁ |
|---|---|---|
| C₂H₅S— | HO— | CH₃— |
| H— | HO— | CH₃— |
| HO— | H— | CH₃— |
| HO— | CH₃O— | CH₃— |
| HO— | C₂H₅— | CH₃— |
| HO— | H₂— | CH₃— |
| HO— | CH₃S— | CH₃— |
| HO— | C₂H₅S— | CH₃— |
| HO— | HO— | CH₃— |
| HO— | HO— | C₂H₅— |
| HO— | HO— | HOCH₂— |
| HO— | HO— | HOCH₂— |
| HO— | HO— | H₃H₇— |
| HO— | HO— | C₃H₃— |
| HO— | HO— | ClCH₂— |
| HO— | HO— | ClCH₂CH₂— |
| HO— | HO— | BrCH₂— |
| HO— | HO— | BrCH₂CH₂— |
| HO— | HO— | NH₂CH₂— |
| HO— | HO— | CH₃COCH₂ (with C=O) |

We claim:

1. A process for preparing a compound having the formula

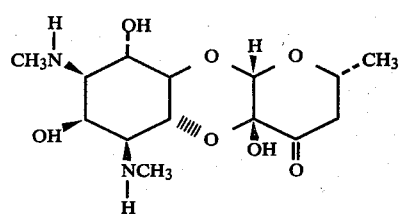

which comprises reacting a compound having the formula

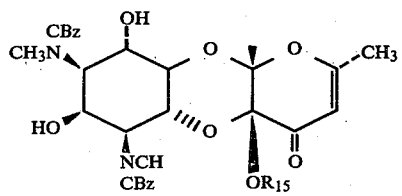

with hydrogen in the presence of a base wherein $R_{15}$ is acyl or hydrogen and CBz is carbobenzyloxy.

2. A process according to claim 1 wherein $R_{15}$ is hydrogen.

3. A process according to claim 1 wherein $R_{15}$ is acyl.

4. A process according to claim 3 wherein acyl is acetyl.

* * * * *

UNITED STATES PATENT OFFICE
CERTIFICATE OF CORRECTION

Patent No. 4,420,624   Dated December 13, 1983

Inventor(s) David R. White & Richard C. Thomas

It is certified that error appears in the above-identified patent and that said Letters Patent are hereby corrected as shown below:

Column 1, lines 27-28 " 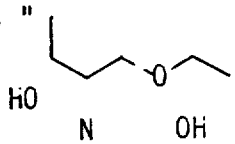 " should read -- 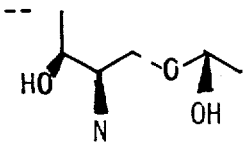 --.

Column 4, line 55 "hydroxy" should read -- hydroxyl --.

Column 5, line 26 " 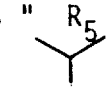 " should read --  --.

Column 5, line 30 " 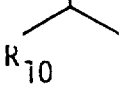 " should read -- 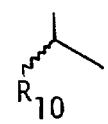 --.

Column 5, line 55 " $R'_8$, $R'_{12}$ " should read -- $R'_8$, $R'_{11}$ and $R'_{12}$ --.

Column 6, line 13 "  " should read --  --.

Column 6, line 30 " 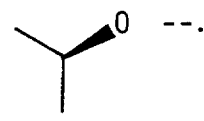 " should read --  --.

Column 7, line 11 " wlerein" should read -- wherein --.

Column 8, line 45 " 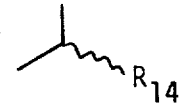 " should read -- 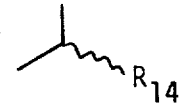 --.

UNITED STATES PATENT OFFICE
CERTIFICATE OF CORRECTION

Patent No. 4,420,624  Dated December 13, 1983

Inventor(s) David R. White & Richard C. Thomas

It is certified that error appears in the above-identified patent and that said Letters Patent are hereby corrected as shown below:

Column 9, line 24 "  " should read --  --.

Column 9, line 55 "CH$_2$CHO" should read -- CH$_3$CHO --.
Column 10, line 1 "CH$_2$CHO" should read -- CH$_3$CHO --.
Column 10, line 55 "CH$_2$CHO" should read -- CH$_3$CHO --.
Column 11, line 7 "IIIb" should read -- IIIb' --.
Column 13, line 23 "vacue" should read -- vacuo --.
Column 15, line 40 "acid as" should read -- acid such as --.
Column 19, line 15 "-4'-O-acetyl" should read -- -4'-di-O-acetyl --.
Column 20, line 20 "FMR" should read -- PMR --.

Column 20, line 35 "  OH " should read --  OH --.

Column 20, line 43 "  " should read --  DMF --.

Column 23, line 56 "acetvl" should read -- acetyl --.
Column 24, line 61 "3'4'-O-" should read -- 3',4'-di-O- --.
Column 26, line 26 "  " should read --  --.

Column 30, line 52 "bicarbonate 15 for 6 days" should read -- bicarbonate for 6 days --.

Column 33, lines 56-57 " 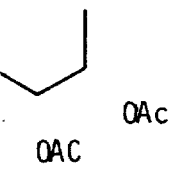 " should read -- 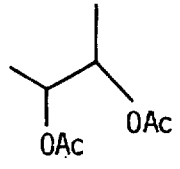 --.

UNITED STATES PATENT OFFICE
CERTIFICATE OF CORRECTION

Patent No. 4,420,624  Dated December 13, 1983

Inventor(s) David R. White and Richard C. Thomas

It is certified that error appears in the above-identified patent and that said Letters Patent are hereby corrected as shown below:

Column 34, line 47 "N,N'dicarbobenzyloxy" should read -- N,N'-dicarbobenzyloxy --.
Column 34, line 58 "1.37 b" should read -- 1.37 g --.
Column 40, line 10 "δ enol ethers for δ enol" should read -- β enol ethers for β enol --.
Column 47, line 47 "dicarbobenzyl" should read -- dicarbobenzyloxy --.
Column 48, line 4, Table XV "  " should read -- 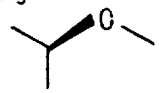 --.

Column 50, line 14 "  " should read -- 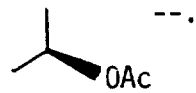 --.

Column 50, line 43 "Pf" should read -- Rf --.
Column 51, lines 8 & 10 "  " should read -- 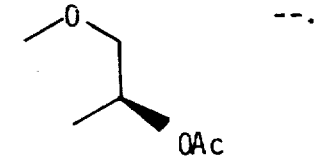 --.

Column 51, line 35 "84-90%" should read -- 85-90% --.
Column 56, line 13 "in in 5 mL" should read -- in 5mL --.
Column 56, line 55, Table XVII "H- $CH_3OCH_2$-" should read -- $CH_3OCH_2$-H- --.

UNITED STATES PATENT OFFICE
CERTIFICATE OF CORRECTION

Patent No. 4,420,624    Dated December 13, 1983

Inventor(s) David R. White & Richard C. Thomas

It is certified that error appears in the above-identified patent and that said Letters Patent are hereby corrected as shown below:

Column 59, line 50, Table XX "  " should read -- -- .

Signed and Sealed this

Ninth Day of December, 1986

*Attest:*

DONALD J. QUIGG

*Attesting Officer*    *Commissioner of Patents and Trademarks*